United States Patent
Stewart et al.

(10) Patent No.: US 6,549,811 B2
(45) Date of Patent: Apr. 15, 2003

(54) MEDICAL ELECTRICAL LEAD HAVING CONTROLLED TEXTURE SURFACE AND METHOD OF MAKING SAME

(75) Inventors: Mark T. Stewart, Lino Lakes, MN (US); Vernon B. Iverson, Elk River, MN (US); Kenneth W. Keeney, Forest Lake, MN (US); Catherine E. Taylor, Minneapolis, MN (US)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 09/760,077

(22) Filed: Jan. 12, 2001

(65) Prior Publication Data

US 2001/0029395 A1 Oct. 11, 2001

Related U.S. Application Data

(63) Continuation of application No. 09/258,515, filed on Feb. 26, 1999, now Pat. No. 6,263,249.
(60) Provisional application No. 60/109,060, filed on Nov. 19, 1998.

(51) Int. Cl.[7] .................................................. A61N 1/05
(52) U.S. Cl. ...................... 607/116; 29/592.1; 427/257; 427/275
(58) Field of Search ................................. 607/115, 116, 607/119, 120–122; 606/41; 600/372, 381; 29/592.1; 427/2.24, 2.25, 452, 257, 275

(56) References Cited

U.S. PATENT DOCUMENTS

| 4,261,806 A | 4/1981 | Asai et al. .................. 204/165 |
| 4,379,459 A | 4/1983 | Stein ..................... 128/419 PG |
| 4,476,868 A | 10/1984 | Thompson ............ 128/419 PG |
| 4,488,954 A | 12/1984 | Chloe et al. ................. 204/169 |
| 4,556,063 A | 12/1985 | Thompson et al. ......... 364/200 |
| 4,692,347 A | 9/1987 | Yasuda ....................... 427/40 |
| 4,718,907 A | 1/1988 | Karwoski et al. .............. 623/12 |
| 4,752,426 A | 6/1988 | Cho ............................. 264/22 |
| 4,821,723 A | 4/1989 | Baker, Jr. et al. ....... 128/419 D |
| 4,846,101 A | 7/1989 | Montgomery et al. ....... 118/723 |
| 4,927,676 A | 5/1990 | Williams et al. .............. 428/36 |
| 4,948,628 A | 8/1990 | Montgomery et al. ........ 427/39 |
| 5,011,494 A | 4/1991 | von Recum et al. .......... 623/11 |
| 5,131,388 A | 7/1992 | Pless et al. ............. 128/419 D |
| 5,133,422 A | 7/1992 | Coury et al. ................. 128/784 |
| 5,133,986 A | 7/1992 | Blum et al. .................... 427/39 |
| 5,144,949 A | 9/1992 | Olson ................... 128/419 PG |
| 5,158,078 A | 10/1992 | Bennett et al. ....... 128/419 PG |

(List continued on next page.)

OTHER PUBLICATIONS

Allmer, K., et al., J. of Polymer Science, vol. 28: pp 173–183 (1990).
Brauker, J.H., et al.,, J. Biomed Mater. Res., 29 (12) pp. 1517–1524 (Dec. 1995).
D'Agostino, R., Academic Press (San Diego, CA) (1990) Title page and Table of Contents only.
Gombotz and Hoffman,, CRC Critical Reviews in Biocompatibility: 4:1, pp. 1–42 (1987).
Ikada, J.,, Biomaterials, 15 pp. 725–736 (1994).
Kulik, F.A., et al., J. of Polymer Science: Part A: Polymer Chemistry, vol. 33:323–330 (1995).

(List continued on next page.)

Primary Examiner—Jeffrey R. Jastrzab
(74) Attorney, Agent, or Firm—Kenneth J. Collier; Girma Wolde-Michael; Tom Berry

(57) ABSTRACT

An elongate elastomeric structure having controlled surface texture. Plasma deposition is used to create controlled features, such as ridges, on the external surface of an elongate elastomeric surface, such as the external surface of silicone tubing. The invention has particular applicability in the medical device field, such as the fabrication of implantable leads, catheters, and medical devices incorporating them.

29 Claims, 22 Drawing Sheets

U.S. PATENT DOCUMENTS

| | | | |
|---|---|---|---|
| 5,199,428 A | 4/1993 | Obel et al. | 128/419 C |
| 5,207,218 A | 5/1993 | Carpentier et al. | 128/419 PG |
| 5,219,361 A | 6/1993 | von Recum et al. | 623/11 |
| 5,223,308 A | 6/1993 | Doehler | 427/575 |
| 5,244,654 A | 9/1993 | Narayanan | 424/78.17 |
| 5,312,453 A | 5/1994 | Shelton et al. | 607/19 |
| 5,314,430 A | 5/1994 | Bardy | 507/5 |
| 5,330,507 A | 7/1994 | Schwartz | 607/14 |
| 5,331,966 A | 7/1994 | Bennett et al. | 128/696 |
| 5,354,316 A | 10/1994 | Keimel | 607/15 |
| 5,411,550 A * | 5/1995 | Herweck et al. | 623/1.27 |
| 5,545,186 A | 8/1996 | Olson et al. | 607/14 |
| 5,593,550 A | 1/1997 | Stewart et al. | 204/165 |
| 5,660,728 A | 8/1997 | Saaski et al. | 210/251 |
| 5,702,618 A | 12/1997 | Saaski et al. | 216/2 |
| 5,705,070 A | 1/1998 | Saaski et al. | 210/446 |

OTHER PUBLICATIONS

Lewandowski, J.J.. Et al., ASAIO Transactions, 37:M295–M297 (1991).

Nishimura, N., et al.,, J. of Materials Science Materials in Medicine, 9, pp. 99–102 (1998).

Picha, G.J. et al.,, Artificial Organs, 14 (suppl. 3) pp. 32–37 (1990).

Rowland, S.,, J. of Applied Biomaterials, 6, pp. 1–7 (1995).

Schmidt, J.A. et al.,, Biomaterials, 12, pp. 385–398 (1991).

Sharkawy, A.A., et al.,, J. Biomed Mater. Res., 40, pp 586–597 (1998).

Stahl, J.B., et al.,, J. Vac. Sci Technol. A., 14(3) pp 1761–1765 (1996).

Triolo and Andrade, J. of Biomedical Materials Research, 17, pp 129–147 (1983).

Triolo and Andrade,, J. of Biomedical Materials Research, 17. Pp 149–165 (1983).

von Recum, A.F. et al.,, Tissue Engineering, 2(4) pp 241–253 (1996).

Yasuda, H.,, Academic Press (Orlando, FL) (1985).

* cited by examiner

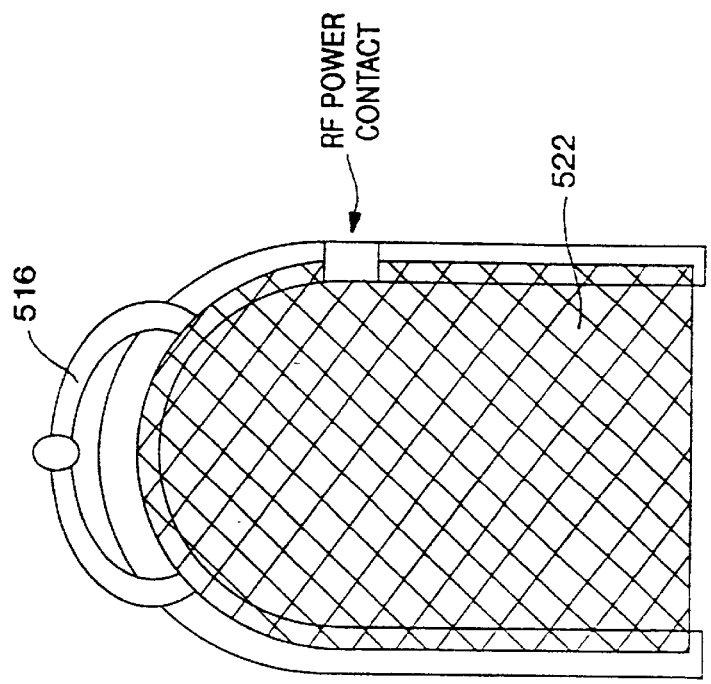
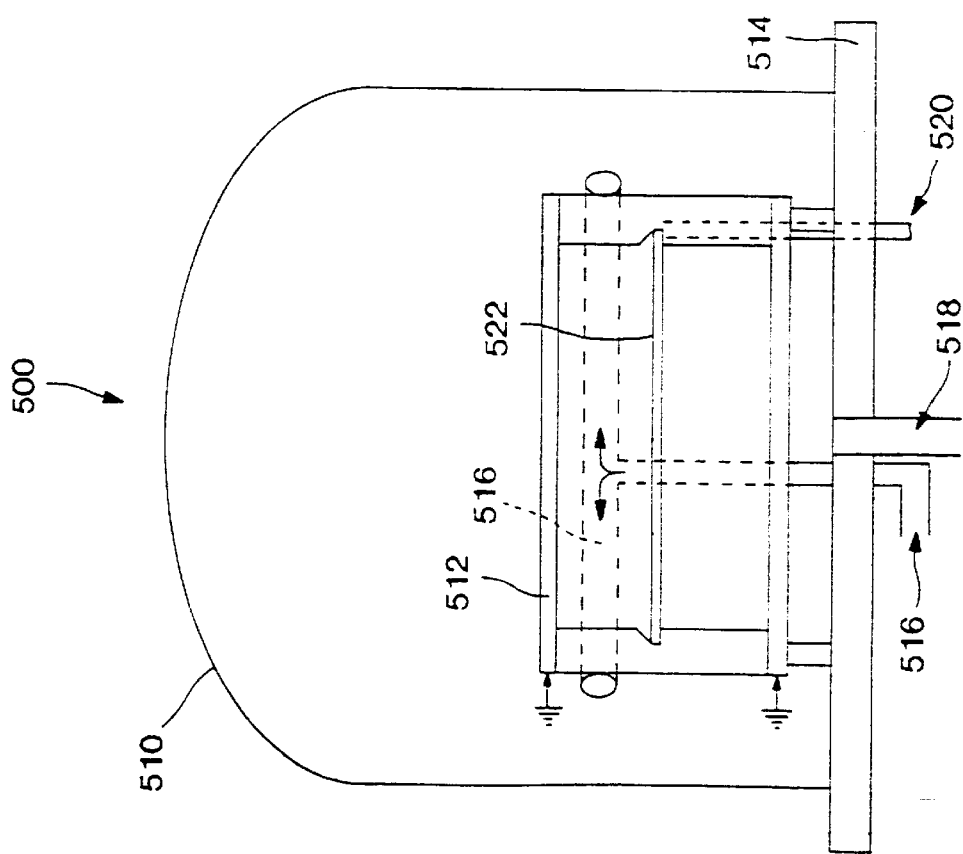
FIG. 10(b)
FIG. 10(a)

MEDICAL ELECTRICAL LEAD HAVING CONTROLLED TEXTURE SURFACE AND METHOD OF MAKING SAME

This application is a Continuation of application Ser. No. 09/258,515 filed Feb. 26, 1999 now U.S. Pat. No. 6,263,249 and Ser. No. 60/109,060 filed Nov. 9, 1998.

FIELD OF THE INVENTION

The present invention relates to a plasma deposition method for forming texture on elastomer surfaces, particularly elongate elastomer surfaces such as the external surface of silicone tubing. The textured surfaces are useful on devices intended for in vivo implantation, such as within a human body.

BACKGROUND

In many medical situations, it is desirable and often necessary to implant medical devices that incorporate elongate structures. For example, elastomeric polymeric tubing, typically having a small diameter, is used in many medical applications and devices. Silicone rubber, especially cross linked silicone elastomer with silica filling, is the polymer of choice for fabricating tubing for use in many medical applications involving implantation. Other suitable elastomeric polymers include polyurethane, polyvinylchloride, polyesters and polyamides.

Implantable elongate elastomeric structures are typified by leads and catheters. Catheters prepared from elastomeric polymeric materials are used frequently in such routine procedures as the intravenous delivery of fluids, removal or drainage of urine or other fluids from compromised patients, chemical sensing using a variety of chemical transducers, monitoring cardiovascular dynamics, and treating cardiac and vascular disorders. Catheters provide the pathway to previously inaccessible body areas for both diagnostic and therapeutic procedures, thereby reducing the need for surgery. For example, double catheter systems are utilized for drug delivery or occlusion of blood flow to specific organs or tissues. In such procedures a rigid outer catheter and a buoyant, flexible inner catheter that can freely float in the blood stream are typically.

Examples of leads include cardiac pacing leads, tachycardia leads, and neurological leads. For example, a pacing lead utilizes a small diameter tubing such as less than 0.055 inch (1.40 mm) (OD) with an inner diameter (ID) of 0.35 inch (0.9 mm). In this type of lead, an elongate wire core (usually in the form of a coil) having a helical screw-in electrode at its distal end is placed inside small diameter tubing to provide a catheter-like device. The core wire is manipulated at the proximal end of this arrangement by the physician during implantation to screw the helical electrode into heart tissue and fix the lead in place.

As catheterization techniques have become more complicated, more demands placed on the performance of the catheter have increased. For instance, the paths that these catheters must take through the body are often long and tortuous, such as accessing the cranial vessels via the femoral artery. Silicone rubber tubing is especially useful for these applications because it is flexible, biocompatible, and allows for transfer of torque along its length. However, the polymeric materials from which catheters are made, such as silicone rubber, have a tacky surface upon exposure to an aqueous environment. This causes excessive friction, making placement of the catheter-like device in the body difficult. Further, these friction characteristics also make torque transfer through the tubing difficult thus, for example, making difficult the turning of the core wire which is preferably a torsion coil in the aforementioned "screw in" pacing lead to screw the helical electrode into tissue.

Plasma discharge has been used on polymeric tubing to modify the surface to improve its slip characteristics, but not by creating texture on the external surface of the tubing. For example, U.S. Pat. No. 5,593,550 (Stewart et al.) is directed to a plasma process for improving the slip characteristics of polymeric tubing on its outer diameter (OD) and inner diameter (ID) surfaces. U.S. Pat. No. 5,133,422 (Coury et al.) is directed to improving the slip characteristics of polymeric tubing on its OD surface by plasma treatment in the presence of a gas selected from the group consisting of hydrogen, nitrogen, ammonia, oxygen, carbon dioxide, $C_2F_6$, $C_2F_4$, $C_3F_6$, $C_2H_4C_2H_2$, $CH_4$, and mixtures thereof. U.S. Pat. No. 4,692,347 (Yasuda) is directed to plasma deposition of coatings and to improving blood compatibility on both the OD and the ID surfaces of polymeric tubing by coating it under discharge conditions in a single chamber.

Plasma reactors are well-known in the art, examples of which are described by Yasuda, H., *Plasma Polymerization*, Academic Press (Orlando, Fla., 1985); and d'Agostino, R., *Plasma Deposition, Treatment, and Etching of Polymers*, Academic Press (San Diego, Calif., 1990). Typically, such plasma reactors use wave energy (RF or microwave) to excite plasma.

In general, a plasma reactor includes a glass reaction chamber that is fitted with a vacuum exhaust, gas inlets and at least one capacitively coupled electrode. In addition, the reactor is fitted with a pressure transducer and a mass flow controller for controlling and measuring the amount of gas being introduced into the reactor. The theory and practice of radio frequency (RF) gas discharge is explained in detail in 1) "Gas-Discharge Techniques For Biomaterial Modifications" by Gombatz and Hoffman, *CRC Critical Reviews in Biocompatibility*, Vol. 4, Issue 1 (1987) pp 1–42; 2) "Surface Modification and Evaluation of Some Commonly Used Catheter Materials I Surface Properties" by Triolo and Andrade, *Journal of Biomedical Materials Research*, Vol. 17, 129–147 (1983), and 3) "Surface Modification and Evaluation of Some Commonly Used Catheter Materials, II. Friction Characterized" also by Triolo and Andrade, *Journal of Biomedical Materials Research*, Vol. 17, 149–165 (1983).

Texturing of silicone surfaces has been achieved by transfer molding (photolithography) wherein a pattern is pressed into the silicone prior to curing. For example, flat stock silicone has been microtextured on one side by curing it on a microtextured glass mask or silicon wafer surface (J. Schmidt et al., *Biomaterials* 12, 385–389 (1991); patents describing this technology include (U.S. Pat. Nos. 5,219,361 and 5,011,494). However, transfer molding has not been used to create controlled texture on the external surfaces of elongate elastomeric structures; it is limited to planar-dimensional texturing. Microtexture on polyoxymethylene, PTFE and polyurethane surfaces has been achieved by natural ion bombardment etching (see von Recum et al., *Tissue Engineering* 2, 241–253 (1996)), however these surfaces are characterized by surface features having random size and distribution, rather than controlled texture comprising a deliberate array of surface features. Thermal evaporation has been used to form a random array of single-crystalline whiskers uniformly oriented with their long axes normal to the a polyimide substrate (J. Stahl et al., *J. Vac. Sci. Technol.* 14, 1761–1765 (1996)).

A number of patents have been reviewed in which plasma reactors are disclosed which use wave energy (RF or microwave) to excite plasma. Although not admitted as prior art, examples of plasma reactors and methods using the same can be found in the issued U.S. patents listed in Table 1 below.

| LIST OF U.S. patents | | |
|---|---|---|
| U.S. 5,593,550 | 01/14/1997 | Stewart et al. |
| U.S. 5,244,654 | 09/14/1993 | Narayanan |
| U.S. 5,223,308 | 06/29/1993 | Doehler |
| U.S. 5,133,986 | 07/28/1992 | Blum et al. |
| U.S. 5,133,422 | 07/28/1992 | Coury et al. |
| U.S. 4,948,628 | 08/14/1990 | Montgomery et al. |
| U.S. 4,927,676 | 05/22/1990 | Williams et al. |
| U.S. 4,846,101 | 07/11/1989 | Montgomery et al. |
| U.S. 4,752,426 | 06/21/1988 | Cho |
| U.S. 4,718,907 | 01/12/1988 | Karwoski et al. |
| U.S. 4,692,347 | 09/08/1987 | Yasuda |
| U.S. 4,488,954 | 12/18/1984 | Choe et al. |
| U.S. 4,261,806 | 04/14/1981 | Asai et al. |

The presence of surface texture may also be important for biocompatibility of medical devices, thus methods for controlling surface texture are potentially useful in controlling tissue responses to biomaterials. For example, the use of tubing having a textured surface may help limit the growth of collagenous tissue around implanted medical devices (e.g. U.S. Pat. No. 5,219,361, von Recum et al.). The ability to provide texture on the external surface of elongate elastomeric materials such as ribbons or tubing would also allow for greater manipulation of surface friction parameters.

Current texturing methods are, however, impractical for achieving texture, particularly microtexture characterized by controlled spacing of surface features, on nonplanar surfaces such as long continuous lengths of tubing surfaces, especially silicone surfaces. It is not possible to use transfer molding to form small patterns on the surface of nonplanar materials, such as long lengths of tubing. Ion beam etching does not allow for controlled or patterned spacing of surface features and, moreover, has not been demonstrated on silicone surfaces. There is, therefore, a need for a process of forming controlled microtexture on an elongate elastomeric surface.

SUMMARY OF THE INVENTION

Although this invention is generally applicable to surfaces of polymeric materials and dielectric materials, especially surfaces of elastomeric materials, it will be described herein with particular reference to silicone surfaces, more particularly nonplanar silicone surfaces such as silicone rubber tubing, but also silicone ribbons and silicone flat stock, all of which are representative of preferred embodiments of the invention.

The present invention has certain objects. That is, various embodiments of the present invention provide solutions to one or more problems existing in the prior art respecting the surface characteristics of elastomeric structures, especially elongate elastomeric structures such as tubing used in medical devices as catheters and leads. These problems include:

(1) lack of an effective method for texturing nonplanar surfaces of elastomeric structures, such as silicone tubing;

(2) growth of collagenous tissue around an implanted device having a smooth surface, such as a lead;

(3) difficulty in handling elastomeric structures having tacky surfaces, such as those fabricated from silicone; and (4) problems with bondability of elongate elastomeric surfaces using adhesives and molding compounds.

It has been discovered according to this invention that plasma deposition can be used to accomplish microtexturing of the external surfaces of elastomeric substrates or materials, including elongate elastomeric articles such as tubing or ribbon. In one embodiment of the invention, texturing takes the form of raised elongate surface features, e.g., ridges, that typically are, but need not, be substantially perpendicular to an axis of the elastomeric material. That is, most of the ridges that make up a surface texture according to the present invention are perpendicular or nearly perpendicular to an axis of the elastomeric material, such that on the whole, the ridges that make up the surface texture appear as a group to be oriented in a direction that is perpendicular to the axis. In most cases, the surface can be examined visually and need not be the subject of quantitative measurement; the directionality of the ridges is typically readily apparent under magnification that is sufficient to distinguish them.

For example, elastomeric material can be subjected to a tension so as to stretch it prior to deposition of the surface texture; that is, plasma is deposited onto the prestretched substrate under tension to achieve surface texture. In the case of elongate material such as tubing or ribbon, the tension is preferably constant and is applied so as to stretch the tubing or ribbon longitudinally. The prestretched tubing is moved through the plasma deposition chamber in a continuous process under constant tension at a defined line speed, and raised ridges are formed that are typically roughly perpendicular to the longitudinal axis of the elastomeric material.

In the case of a planar sheet of elastomeric material, tension can be applied to stretch the sheet, for example, by pulling on opposite sides of a sheet, or by securing one side and pulling on the opposite side, thereby defining an axis extending from one side of the sheet to the opposite side of the sheet. In a preferred embodiment of the invention flat substrate is stretched along such axis prior to plasma deposition of the surface texture in a batch process, such that controlled a surface texture, comprising for example raised ridges, is formed on the prestretched surface. Alternatively, the surface texture can be plasma deposited on the unstretched surface of a planar elastomeric substrate, in which event the surface texture is typically more disordered. In addition, surface features produced by texturing unstretched planar substrates can show a radial distribution pattern around surface flaws on the substrate surface.

Surface texture formed on elastomeric substrates according to the invention can further take the form of irregularly shaped micronodules or bumps instead of, or in addition to, raised elongate structures such as ridges.

The surface features that form the textured elastomeric surfaces of the invention are micron scale; that is, as a whole, the dimensions of the features (i.e., width, height and spacing) typically fall within the range from about 0.01 micron to about 100 microns. When the surface features take an elongate form, such as ridges, the length of the surface features can be even longer; thus the term "micron scale surface features" includes elongate surface features having widths, heights and crest-to-crest distances that fall within the range of about 0.01 micron to about 100 microns, even though their lengths may be greater than 100 microns.

Textured external surfaces of elastomeric materials of the invention are preferably characterized by controlled spacing of the surface features, such as ridges or micronodules. Control of feature spacing is achieved by manipulating the tension and/or, where applicable, line speed plasma deposition parameters to achieve the desired feature spacing. For example, in the case of elongate elastomeric materials, spacing of the features relative to the longitudinal axis of the elongate elastomeric substrate is controlled during the plasma deposition process by manipulating the tension applied to the elongate material and/or the transport line speed at which it moves through the deposition chamber. Typically the tension and line speed remain constant during a plasma deposition run, but there may be applications in which one or both of these parameters are manipulated during plasma deposition, for example, to produce tubing with different feature spacing along discrete sections of one continuous length.

Using elastomeric tubing as an example, the tubing is typically first cleaned, then spooled and placed in the plasma reactor. The tubing is continuously drawn through a glass reactor or other plasma discharge chamber (preferably thick walled glass or a suitable ceramic) which receives the tubing longitudinally from a coil or spool inside an adjacent vacuum chamber such as a bell jar. Typically, the line speed and the tension that is applied to the elongate elastomeric material are controlled by a closed loop proportional integral and derivative (PID) feedback system. This system uses an optical encoder (i.e., a laser pulse counting diode) connected to the lower drive motor to control the tubing speed, and a load cell interlocked to an upper drive motor to control tension. When the transport speed of the lower motor is established, the upper motor increases or decreases its speed to maintain the proper tension. Line speed can be monitored using a laser directed through slots cut into the change-of-direction pulley. A monomer is discharged in the glass reactor, and the tubing tension and line speed are controlled such that the monomer is deposited on the tubing to form texture on at least one external surface of the material.

The texture typically takes the form of a series of substantially parallel raised elongate structures, which appear as nodular or rounded ridges of deposited materials having crest-to-crest distances on the micron scale, the ridges being roughly perpendicular to the longitudinal axis of the elongate material as described above. That is, on the whole, the ridges that make up the surface texture appear as a group to parallel to each other, although signification deviation from true parallelism is typical and acceptable. In most cases, the surface can be inspected visually and need not be the subject of quantitative measurement; the directionality of the ridges is typically readily apparent under magnification that is sufficient to distinguish them. The height of a ridge can vary along its length.

In the case of tubing, these ridges can, but often do not, extend around the entire circumference of the tubing; however, they typically transcribe at least an arc substantially along a circumference of the tubing.

Generally, any electrically non-conductive dielectric reactor chamber means which holds a vacuum will suffice as a discharge chamber. Typically, the discharge chamber is a glass chamber. In the case of tubing material, the shape of the discharge chamber is preferably tubular. Surface texture can be applied to tubing or ribbon of virtually any size diameter or width, respectively. Texture can be applied to the external surface of virtually unlimited lengths of tubing or ribbon; the only limitation is how large a spool can be fitted inside of the vacuum chamber. A typical reactor will have a capacity of 1,000 to about 5,000 feet depending on the tubing diameter or ribbon width.

The absolute size of the space relationship between the external surface of the polymer tubing or ribbon and the internal dimensions the discharge chamber in which plasma deposition is accomplished in any given instance will depend on many variables e.g., gas pressure, power applied, relative size of space in the glass tube and the size of the polymeric tubing, and so forth.

As an example, the following treatment conditions provide silicone tubing with a textured outer surface according to the invention: external diameter of the glass tube (discharge chamber) of about 1 to about 2 inches; the length of the glass tube from about 6 inches to about 26 inches; RF power of about 30 watts to about 300 watts, applied in a continuous power mode; gas pressure in the plasma reactor of 0.010 Torr to about 5 Torr; tubing tension of about 5 grams to about 100 grams; and line speed of about 5 inches per minute to about 100 inches per minute. In any given instance, it can be readily determined empirically by varying discharge conditions and time of exposure to discharge as to what surface treatment results are obtained, then adjusting the conditions to obtain the desired result; see Example II. Moreover, operating parameters can be readily manipulated by one skilled in the art to achieve optimal reaction conditions for plasma deposition to form a textured surface on non-silicone prestretched elastomeric tubing.

Optionally, the external surface of the tubing or ribbon can be plasma pretreated prior to plasma deposition of the surface texture. Pretreatment can improve adherence of the monomer to the tubing surface when they are "unlike" substances, for example when fluorocarbon monomers are plasma deposited onto polyurethane surfaces, or amine-containing monomers are plasma deposited onto silicone surfaces. Typically, when the monomer and the surfaces are "like" substances, such as when siloxane monomers are deposited onto a silicone surface, they adhere sufficiently without plasma pretreatment. In embodiments of the invention that include plasma pretreating the elastomeric material prior to plasma deposition, the plasma reactor has at least two zones: a plasma pretreatment zone and a surface texturing zone, each having a glass reactor or plasma discharge chamber and its own set of electrodes and RF power source (see copending commonly assigned U.S. patent application Ser. No 08/923,046). For purposes of plasma pretreatment, the gas discharge process or radio frequency discharge as contemplated herein need only be such as to give rise to a plasma glow discharge which interacts with surfaces exposed thereto, such as silicone rubber, to alter same by reaction therewith. The plasma discharge apparatus thus includes a radio frequency power source, a matching network to electronically balance forward and reflected power, and cables and electrodes to deliver power to the reactor and ignite the plasma. In this embodiment the tubing or ribbon is first drawn through the plasma pretreatment zone where glow discharge electrodes are applied to the glass reactor or discharge chamber with the plasma discharge gas being inside the glass reactor. The tubing or ribbon then passes through a transition zone, then into surface texturing zone where monomer is deposited on the pretreated external surface of the tubing according to the invention.

The term "tubing" as used herein means an elongate cylindrical structure having one or more lumens extending along its length. Each lumen defines an inner diameter (ID) surface of the tubing. For some applications it is desirable to plasma deposit a film on the inner diameter ID surface of elastomeric tubing (see, e.g., U.S. Pat. No. 5,593,550). The present invention allows for plasma deposition on the ID surface of tubing either before or after surface texturing. If film is to be deposited on the ID surface of the tubing, the plasma reactor further includes an ID monomer deposition zone having a glass reactor or discharge chamber and its own set of electrodes and RF power source, such as that shown in U.S. Pat. No. 5,593,550 and copending commonly assigned application Ser. No 08/923,046. When plasma depositing a polymerized film on an ID surface of tubing, it is advantageous for the external surface of the tubing to be slippery since the cylindrical glass reactor used in the ID monomer deposition zone must be in very close proximity to the external surface of the tubing. If the external surface of the tubing is not plasma pretreated, then the surface texturing zone as described herein is preferably situated before the ID monomer deposition zone, since surface texturing makes the external surface more slippery. On the other hand, if the external surface of the tubing is already plasma pretreated (which improves its slip characteristics) the ID monomer deposition zone can be situated either before or after the surface texturing zone according to the invention. Preferably, however, the ID monomer deposition zone is situated after the surface texturing zone.

Also optionally, the plasma reactor can have a monomer deposition zone for additional plasma deposition onto the external surface of the tubing or ribbon either prior to or subsequent to surface texturing. This additional monomer deposition zone deposition includes a glass reactor or monomer deposition chamber and its own set of electrodes and RF power source. As in the glow discharge chamber used in the optional plasma pretreatment process, the monomer deposition chamber includes electric reactor for connection to a radio frequency power source or the like for activation of the monomer upon application of power and exposure to a monomer vapor from a monomer source. When the monomer deposition zone is situated after the surface texturing zone, the additional plasma deposited on the textured external surface of the tubing or ribbon must form a very thin layer. Preferably, the coating has a thickness of about 1 nm to about 1 μm so as not to obscure or obliterate the surface texture by filling in the spaces between the ridges or nodules. Accordingly, the film that is plasma deposited in this zone preferably forms a monolayer, i.e., a layer that having a depth of about one molecule, on the external surface of the elongate elastomeric material.

The textured elastomeric material optionally incorporates a bioactive molecule into its external surface or, in the case of tubing, into its internal surface, or both. For example, the monomer deposited to create the texture can contain activated groups for subsequent covalent attachment of a bioactive monomer. Likewise, a monolayer that is plasma deposited onto the external surface of the elongate elastomeric material after texturing can include such activated groups. The internal surface of tubing can also be activated by plasma depositing onto the internal surface a monomer that contains such activated groups. Covalent attachment of the bioactive molecule to the activated internal or external surface of the elongate elastomeric material is typically accomplished by dipping the material into a solution that contains the bioactive molecule, which may itself be activated or modified so as to react with the activated internal or external surface of the material, but any convenient method for contacting the biomolecule with the activated surface of the material can be used.

If the elongate elastomeric material is externally coated after surface texturing according to the invention, for example by dipping or spraying, care must be taken to insure that the coating layer is very thin, preferably a monolayer, so as not to obscure or obliterate the surface texturing by filling in the spaces between the ridges on the external surface of the material.

Various embodiments of the present invention thus have the object of solving at least one of the problems associated with prior art devices. Texture on an external polymer surface inhibits the growth of collagenous tissue around an implanted device. In the case of bradycardia and tachyarrhythmia pacing and defibrillation leads, the control of fibrous capsule growth could significantly improve chronic removability; tissue ingrowth around conventional leads that have been implanted for some time can make removal of failed leads extremely difficult.

Moreover, in many applications it is desirable to provide a lubricious external surface on the elongate elastomeric material in order to reduce surface friction or tackiness that results when the material is exposed to aqueous environments, such as an in vivo environment. An important goal of the present invention to improve the slip characteristics of elastomeric tubing, and it has been surprisingly found that texturing the external surface of silicone tubing in accordance with the invention renders them less tacky and more manageable. Additionally, it is expected that the application of surface texture to silicone tubing in accordance with the invention will yield silicone tubing that is more manageable in the hands of the physician compared to tubing whose slip characteristics have been altered by other methods.

Surface texturing also improves surface bonding characteristics with respect to adhesives and molding compounds, which is advantageous, for example, at the terminal ends of leads.

The present method for forming controlled features on a length of elongate elastomeric material is far superior to transfer molding. Various embodiments of the plasma deposition method of the present invention provide one or more of the following advantages: (a) the method allows deposition of cross-linked siloxane coatings on the surface of silicone tubing, forming specific sized surface features; (b) the method has the ability to deposit these coatings on continuous lengths of tubing, for example tubing exceeding 1000 feet; (c) the coatings are deposited using a vacuum system and a RF plasma deposition zone; and (d) the method allows for control of the randomness or linearity of the deposited ridge features using selected process parameters.

Some of the embodiments of the invention include one or more of the following features: (a) controlled surface feature spacing, for example on the external surface of a continuous length of silicone tubing, ribbon or sheet; (b) micron scale raised nodules or ridges on an external surface of an elastomeric substrate; (c) a textured external elastomeric surface having the ability to limit or control the growth of collagenous tissue when used in vivo; (d) cross-linked siloxane coatings on the surface of silicone tubing with specific sized surface features; (e) a textured external silicone surface having improved slip characteristics.

BRIEF DESCRIPTION OF THE DRAWINGS

FIGS. 10A and 10B show an RF-powered parallel plate batch process plasma reactor that allows depositing of a monomer to form surface texture on prestretched elastomeric flat stock.

DETAILED DESCRIPTION

Figure 1A:
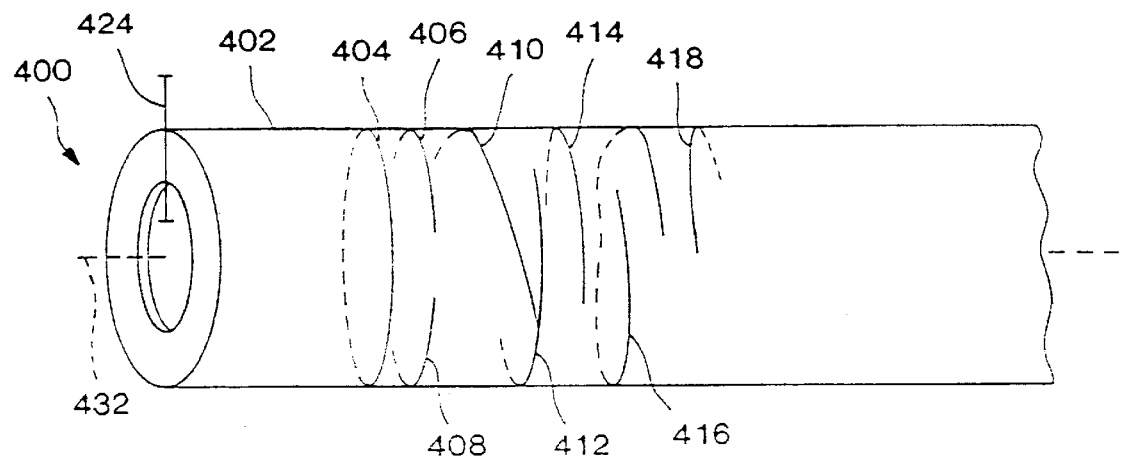
FIGS. 1A and 1B depict textured elastomeric tubing showing (a) a textured external tubing surface characterized by raised ridges and (b) longitudinal cross section of the external textured tubing surface showing raised ridges in detail.

Texture is formed on an elastomeric surface according to the present invention by plasma deposition of a reactant monomer. As used herein, the term "reactant monomer" refers to a branched or unbranched hydrocarbon that can be plasma deposited on a substrate, preferably at a relatively low temperature. The hydrocarbon can contain one or more aliphatic groups, one or more cyclic groups, or a combination of aliphatic and cyclic groups (e.g., alkaryl and aralkyl groups). The hydrocarbon is not limited to hydrogen and carbon atoms, but may optionally include one or more heteroatom, such as nitrogen, oxygen, sulfur, silicon, etc. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more carbon-carbon triple bonds. The term "cyclic group" means a closed ring hydrocarbon group and includes an alicyclic group, an aromatic group, and a heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a cyclic hydrocarbon group that contains a heteroatom such as nitrogen, oxygen, sulfur, silicon, etc.

Preferred reactant monomers used in the plasma deposition method of the present invention include-acetylene, ethylene, xylene, 2-methyl 1-pentene, divinylmethylsilane, trimethylsilane, tetramethylsilane, trimethyidisilane, hexamethyidisilane, hexamethyidisiloxane (HMDSO), tetramethyidisiloxane (TMDSO), hexamethyidisilane, hexamethyidisilazane, tetraethoxysilane, octamethylcyclotetrasiloxane, tetramethylcyclotetrasiloxane, hexamethyltrisiloxane and allyltrimethoxysilane. Siloxanes and silanes are particularly preferred. More preferably, the reactant monomer is a linear or cyclic siloxane, such as hexamethyidisiloxane (HMDSO), tetramethyldisiloxane (TMDSO) octamethylcyclotetrasiloxane, tetramethylcyclotetrasiloxane or hexamethylcyclotrisiloxane.

Many plasma deposition parameters potentially affect plasma deposition on elastomeric surfaces. These parameters include the type of monomer used (e.g., siloxane or silane, linear or cyclic), monomer vapor flow rate, monomer deposition chamber pressure, monomer entry location into deposition chamber, inert co-gas addition to deposition zone, co-gas flow rate, deposition chamber geometry, deposition chamber plasma excitation electrode type, deposition chamber plasma excitation frequency (50 kHz–2.45 GHz), waveform of the plasma excitation energy (pulsed or not), plasma excitation energy pulse duty cycle, plasma excitation energy pulse length, tubing transport line speed through deposition chamber, tubing transport tension, and tubing pre-treatment prior to monomer deposition.

Of these parameters, the present invention focuses on two that were found to particularly affect plasma deposition on elongate elastomeric surfaces such as silicone tubing: tubing tension and tubing transport line speed. Control of these two deposition process parameters allows for controlled feature spacing of ridges that are deposited from a reactant monomer plasma, such as a hexamethyidisiloxane (HMDSO) plasma, onto silicone tubing. Surprisingly, the radio frequency (RF) power delivered to the deposition chamber has little effect on the ridge spacing. Even more surprising is the finding that line speed has more effect on the ridge spacing than do tubing tension and RF power.

In addition, control of the tubing tension parameter alone allows for control of the randomness of the ridged features. With low tension, the ridges weave around but generally are parallel to the transverse axis of the tubing (90 degrees from the longitudinal axis). With higher tension, the ridges were observed to be much straighter in line with the transverse axis of the tubing.

Optionally, the reactant monomer can be deposited on the elastomeric surface in the presence of an inert gas. The inert gas is preferably argon, helium, nitrogen, neon, or a combination thereof. More preferably, the inert gas is argon. Preferred ratios of the reactant monomer to the inert gas depend on reactor geometry and are readily determined by one skilled in the art.

If the OD surface of the elastomeric structure is to be plasma pretreated prior to plasma deposition of the surface texture, the device is contacted with an inert gas in a plasma pretreatment zone prior to depositing a reactant monomer in a surface texturing zone to form the surface texture. For example, to plasma pretreat silicone tubing, inert gas can be supplied at a flow rate of about 1 to about 10 sccm at a pressure of about 5 mTorr to about 5 Torr. Glow discharge of an inert gas such as argon is generated using an R.F. power of about 50 to about 200 watts.

As described above, the method of forming surface texture according to the invention optionally further includes plasma depositing an additional polymer coating on the external surface of the elastomeric material, either before or after plasma deposition of the surface texture. If applied to the external surface after texturing, the polymer coating is sufficiently thin so as to retain some surface texturing on the external surface; preferably, the polymer coating is a monolayer. For example, a textured silicone tubing can be coated with a thin plasma-polymerized hydrocarbon coating to improve the adhesion of urethane adhesives to the textured silicone tubing. A polymer coating can also serve, for example, as a barrier layer for electronic contacts and devices, or as a barrier layer to stop the diffusion of liquid into the tubing lumen or into the device. Prior to texturing, elastomeric material can be coated with, for example, an antimicrobial agent, such as thin metallic silver layer. This allows the slow release of silver ions through the surface texture layer.

As an alternative to plasma deposition of the additional polymer coating, the elongate elastomeric a polymer coating can be applied to the internal or external surface of the tubing using conventional methods such dipping, spraying, or other solution-based application techniques. It should be understood that the elongate elastomeric material can be coated with a polymer either before texturing, or after texturing as long as the resulting material remains textured.

Polymers particularly suitable for use as plasma-deposited or solution coatings or films include a natural hydrogel, a synthetic hydrogel, teflon, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

The method of forming surface texture according to the invention also optionally includes the incorporation of a bioactive compound onto an internal or external surface of the device. In one embodiment, a bioactive compound is applied to an activated surface of the device. Examples of activated surfaces include surfaces containing amine, acid or vinyl functional groups. The surface of the device can be activated, for example, by plasma treatment. Or, the monomer used in plasma deposition to form the desired surface texture can itself contain functional groups capable of covalent reaction with the bioactive compound. For example, the monomer used to create the surface texture can comprise an amine-functionalized silane, and the bioactive compound is, accordingly, one that is capable of covalent linkage with an amine. Yet another way of providing an activated surface involves plasma depositing a very thin layer, preferably a monolayer, of an activated monomer after texturing, taking care so as to avoid obscuring or obliterating the surface texture by filling in the spaces between the raised features. An activated layer can also be provided by dipping the device in a liquid, or spraying the device with a liquid or aerosol, to form of a very thin coating containing a functionalized species for subsequent reaction with the bioactive compound, again taking care not to fill the spaces between the raised features on the external surface of the device. Optionally, an activated layer can be supplied on the non-textured ID surface of the tubing, for example where the ID surface of tubing is likely to come into contact with body tissue or fluid, such as tubing intended to carry blood or plasma, or used in the fabrication of a vascular graft or stent, can be activated. The activated internal surface can be produced by passing a liquid through a length of the tubing lumen to form an internal coating containing the functionalized species for subsequent reaction with the bioactive compound. An activated internal or external surface of the material is then contacted with the bioactive compound under conditions that allow formation of a covalent linkage between molecules on the activated surface, which typically are but not be functionalized molecules, and the bioactive compound, thereby forming an elastomeric material comprising a bioactive compound.

Alternatively, a bioactive compound can be added to a coating mixture prior to applying a very thin coating to the textured surface of the device by dipping or spraying, as described above, in which event the bioactive compound need not be covalently linked to the coating or plasma deposited surface as described above but nonetheless remains on the surface of the device after the coating has dried. Likewise, if the bioactive molecule is to be incorporated into the internal surface of a textured tubing, it can be added to the coating mixture prior to application to the tubing lumen and will remain on the internal surface even though it is not covalently linked to any surface molecules. A bioactive compound that is not covalently attached to a device surface is, optionally, capable of eluting from the surface when the device is in place within a patient's body.

Examples of bioactive compounds include an antibacterial or antimicrobial agent, an anticoagulant agent, an antithrombotic agent, an antiplatelet agent, an antimitotic agent, an antioxidant, an antimetabolite agent, an anti-inflammatory agent, an enzyme, a catalyst, a hormone, a growth factor, a lectin, a therapeutic drug, a vitamin, an antibody, an antigen, a nucleic acid such as DNA and RNA, a protein or peptide, a polysaccharide, a dye, or any combination thereof. For example, one preferred bioactive compound is heparin. The subsequent addition of a polymer and/or a bioactive compound can be accomplished utilizing conventional techniques known in the art, such as described by Y. Ikada, "Surface Modification of Polymers for Medical Applications," *Biomaterials*, Vol. 15:725–736 (1994); E. A. Kulik, et al., "Peroxide Generation and Decomposition on Polymer Surface," *J. of Polymer Science: Part A: Polymer Chemistry*, Vol. 33:323–330 (1995); and K. Allmär et al., *J. of Polymer Science*, Vol. 28:173–183 (1990), for example.

Surface texturing of the elastomeric substrate according to the present invention is preferably accomplished at a relatively low temperature, such that an input of energy to increase the temperature during plasma deposition is not required. In accordance with the present invention, plasma deposition preferably occurs at about ambient temperature, typically from about 20°C. to about 30°C.

The textured surface of the invention is preferably a surface of an elastomeric material or substrate. An-elastomeric material is one that has elastic properties. For example, ribbon or tubing made from an elastomeric material can be stretched or extended to at least double its length, preferably to at least several times its length, then return to its original length when released. Examples of elastomeric materials include polyurethane, silicone, polyisoprene, natural or latex rubber, plasticized polyvinylchloride, elastomeric polyamides, including copolymers comprising elastomeric polyamides, such as PEBAX, elastomeric polyester, polybutadiene and neoprene. Preferably, the elastomeric substrate having texture according to the invention includes polyurethane, silicone, polyisoprene, or natural rubber; more preferably the textured elastomeric material of the invention is a textured silicone.

Structures or articles provide by the invention have at least one external textured surface. A preferred textured structure is an elongate structure, more preferably an elongate elastomeric structure, such as elastomeric tubing or ribbon material. In the case of tubing, the textured surface comprises at least a portion of the OD surface of the tubing; in the case of ribbon, the textured surface includes at least a portion of one or both sides of the ribbon material. Nonetheless, a textured flat substrate, such as a flat sheet of elastomeric material, is also encompassed by the present invention. Preferably, the textured structure is formed from an elastomeric material, preferably silicone flat stock, so that it can be stretched during deposition of the monomers to form the surface texture.

Surface texture as provided by the invention is typified by distinct, raised features on an external surface of the elastomeric substrate. The method of the invention produces surface textures on elastomeric materials that can be uniform or nonuniform; if nonuniform, however, the surface texture is nonetheless preferably characterized by a deliberate array of surface features; in other words, the surface texture is preferably not random. Surface texture provided by the invention can, but need not, have a directionality associated with either of both the longitudinal axis of the material or the axis perpendicular thereto, and can include micron scale ridges, micronodules or raised features of any kind, rounded, flat-topped, or angular. An important feature of the method of the invention is that at least one of the dimensions of the features that form the texture, i.e., the size, shape, height, or directionality of the features (such as the degree of parallelism with the perpendicular to the longitudinal axis of the substrate), the spacing between the features, the relative amount of uniformity or disorder associated with the features, their spacing or relief characteristics, and the like, can be controlled by either or both of a change in tension or line speed during the plasma deposition process. For example, the spacing of surface ridges can be controlled by the tension applied to the elastomeric substrate (i.e., the amount of stretching the material is subjected to prior to plasma deposition of surface texture) and/or, in the case an elongate substrate like tubing or ribbon, line speed. It should be understood that the tension and, in the case of an elongate substrate, line speed needed to achieve surface texturing on an elastomeric substrate will depend on factors such as the nature of the elastomer and, in the case of tubing, the OD of the tubing, the number and dimensions of lumens, and that the appropriate tension and line speed can be readily determined by one in the art in accordance with the Examples set forth below. Textured tubing according to the invention preferably has an OD of about 0.030 to about 0.25 inches although surface texturing can be applied to any diameter tubing as long as the size of the glass deposition chamber is selected to accommodate it.

Figure 1B:
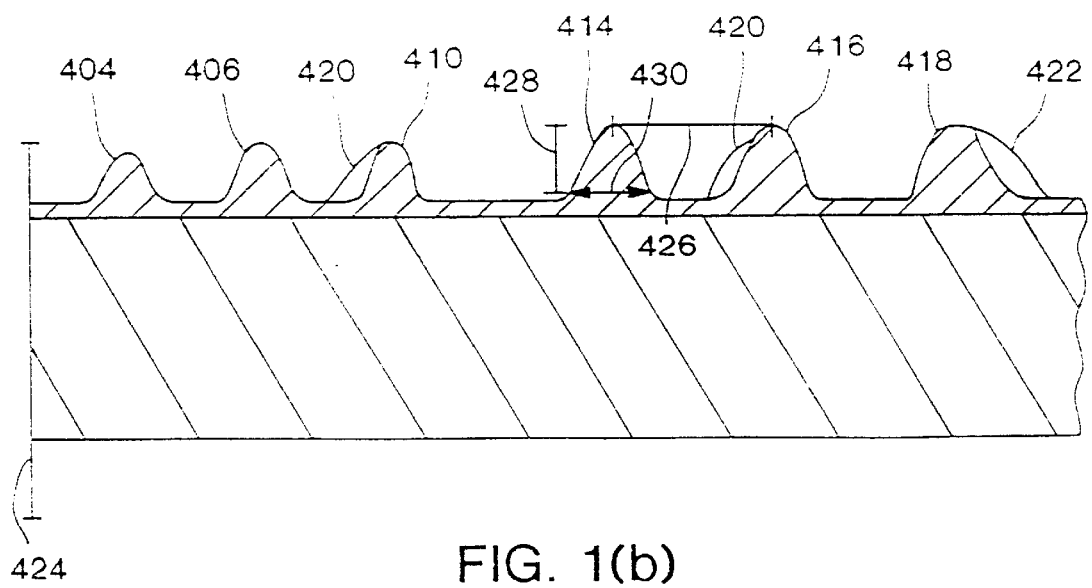

FIG. 1 shows a preferred embodiment of the textured elastomeric material of the invention. Elastomeric tubing 400 has a textured external surface 402 comprising a multiplicity of raised elongate features 404, 406, 408, 410, 412, 414, 416 and 418 (i.e., ridges). Preferably, the arrangement or pattern of the raised features on the surface of the elastomeric substrate has a directionality associated therewith; for example, in some embodiments the textures comprises rounded ridges substantially aligned with the perpendicular to an axis, typically a longitudinal axis, of the substrate. Thus, in FIG. 1, the raised ridges 404, 406, 408, 410, 412, 414, 416 and 418 are roughly perpendicular to the longitudinal axis 432 of tubing 400 and roughly parallel to each other. The crest-to-crest distance 426 between raised ridges is submicron or micron scale, typically ranging from about 0.05 microns to about 100 microns, preferably distance 426 measures about 0.1 micron and about 50 microns; more preferably it measures about 0.5 microns to about 30 microns. The slip characteristics of the external surface of the substrate are improved using ridges separated by distances within the foregoing ranges. For surfaces intended to be placed in contact with body tissue, the distance 426 between raised ridges is preferably about 1 to about 4 microns, and optionally remains relatively constant from ridge to ridge, with a mean value of about 2 to about 3 microns. Optionally, the surface contains micronodules of smaller relief in the areas between the ridges, creating bumpy, largely disordered surface in between the ridges (not shown). The ridges have a peak height 428 measured from the valley portion of the substrate surface to the peak of the ridge that typically ranges from about 0.01 micron to about 5 microns, preferably from about 0.05 microns to about 3 microns, more preferably from about 0.1 microns to about 2 microns. Optionally, the ridge varies in height along its length. The width 430 of the ridges on the tubing is typically about 0.1 micron to about 5 microns, preferably about 0.5 microns to about 2 microns. In the case of surface texture that is plasma deposited onto prestretched planar materials in accordance with the invention, the ridge width is somewhat broader, preferably about 0.5 microns to about 10 microns, more preferably about 1 micron to about 5 microns.

On tubing or ribbon material, a preferred textured surface comprises ridges that are roughly perpendicular to the longitudinal axis 432 of the tubing or ribbon and thus are roughly parallel to one another. Optionally, the ridges are relatively evenly spaced along the length of the longitudinal axis. Ridges, while nonetheless being substantially parallel, can and typically do merge into one another, intersect, or interweave. In the case of tubing, ridges can span all or a portion of the external circumference of the tubing. Non-limiting examples of ridge topography for elastomeric tubing are shown in full view in FIG. 1(a) and in cross section in FIG. 1(b). Ridge 404, which is perpendicular to the longitudinal tubing axis 432, extends around an entire circumference of tubing 400; ridges 404 and 408, parallel to ridge 404, each span a portion of tubing 400 along the same circumference, thus depicting a broken or interrupted circumferential ridge; ridge 410 is slightly offset in the proximal direction from the perpendicular to the longitudinal axis 432 and, for that reason, weaves into ridge 412, which is close to ridge 410 and perpendicular to the longitudinal axis 432; ridge 414 extends around a portion of a circumference of tubing 400; ridge 416 spans more that a single circumference of tubing 400 but is slightly offset in the proximal direction from the perpendicular to the longitudinal axis 432, thus forming a helical ridge; and ridge 418 spans a portion of a circumference of the tubing but is slightly offset in the distal direction from the perpendicular to the longitudinal axis 432. The cross section 424 of tubing 400 allows visualization of external surfaces 420 of ridges 410 and 416 which are proximally offset from the perpendicular to the longitudinal axis 432, and external surface 422 of ridge 418 which is distally offset from the perpendicular to the longitudinal axis 432.

In particularly preferred embodiments of the elastomeric materials having textured surfaces according to the invention, the surface features are relatively evenly spaced. In the case of ridges, the more order there is to the surface texture, that is, the more nearly parallel the ridges are, the more even the spacing between the ridges becomes. Disorder can be measured by the number of ridges that cross a line of given length drawn perpendicular to the longitudinal axis on a photomicrograph of the textured surface, as described in Example II.

An implantable device having a textured elongate elastomeric surface, such as textured silicone rubber tubing, is also included in the invention. Examples of such devices include cardiac pacing leads, tachycardia leads, drug delivery catheters, indwelling drainage catheters, neurological leads, and other devices that incorporate textured leads and catheters as provided by the invention, such as a pacemaker, a pacemaker-cardioverter-defibrillator, an implantable neurostimulator or nerve stimulator, a muscle stimulator, an implantable monitoring device, an implantable fluid handling device, a defibrillator, a cardioverter/defibrillator, a gastric stimulator, a drug pump, and a hemodynamic monitoring device. For example, the implantable device can be a pacemaker such as that described in U.S. Pat. No. 5,158,078 to Bennett, et al.; U.S. Pat. No. 5,312,453 to Shelton et al.; or U.S. Pat. No. 5,144,949 to Olson et al., or a pacemaker-cardioverter-defibrillator (PCD) corresponding to any of the various commercially-available implantable PCDs such as those described in U.S. Pat. No. 5,545,186 to Olson, et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al. Alternatively, an implantable device according to the present invention can be an implantable neurostimulator, nerve stimulator or muscle stimulator such as that disclosed in U.S. Pat. No. 5,199,428 to Obel, et al.; U.S. Pat. No. 5,207,218 to Carpentier, et al.; or U.S. Pat. No. 5,330,507 to Schwartz, or an implantable monitoring device such as that disclosed in U.S. Pat. No. 5,331,966 to Bennett, et al.

Additionally, the implantable device may be micromachined devices such as implantable fluid handling devices for continuous administration of therapeutic agents including those for pain management, cancer chemotherapy, treatment of intractable spasticity, to name a few. Such devices are described in, for example, U.S. Pat. Nos. 5,705,070; 5,702,618; and 5,660,728 all to Saaski et al.

Further, for example, an implanted device may be a defibrillator, a cardioverter/defibrillator, a brain stimulator, a gastric stimulator, a drug pump, a hemodynamic monitoring device, or any other implantable device containing an elongate elastomeric structure. Therefore, the present invention is believed to find wide application in any form of implantable device that makes use of an elongate elastomeric structure. As such, the description herein making reference to any particular medical device is not to be taken as a limitation of the type of medical device envisioned by the present invention.

The implantable device preferably includes at least one textured elastomeric surface wherein the texture is formed thereon from at least one compound selected from the group consisting of acetylene, ethylene, xylene, 2-methyl 1-pentene, divinylmethylsilane, trimethylsilane, tetramethylsilane, trimethyldisilane, hexamethyidisilane, hexamethyidisiloxane (HMDSO), tetramethyidisiloxane (TMDSO), hexamethyidisilane, hexamethyldisilazane, tetraethoxysilane, octamethylcyclotetrasiloxane, tetramethylcyclotetrasiloxane, hexamethyltrisiloxane and allyltrimethoxysilane. Siloxanes and silanes are particularly preferred. More preferably, the reactant monomer is a linear or cyclic siloxane, such as hexamethyidisiloxane (HMDSO), tetramethyldisiloxane (TMDSO) octamethylcyclotetrasiloxane, tetramethylcyclotetrasiloxane or hexamethylcyclotrisiloxane.

Figure 2:
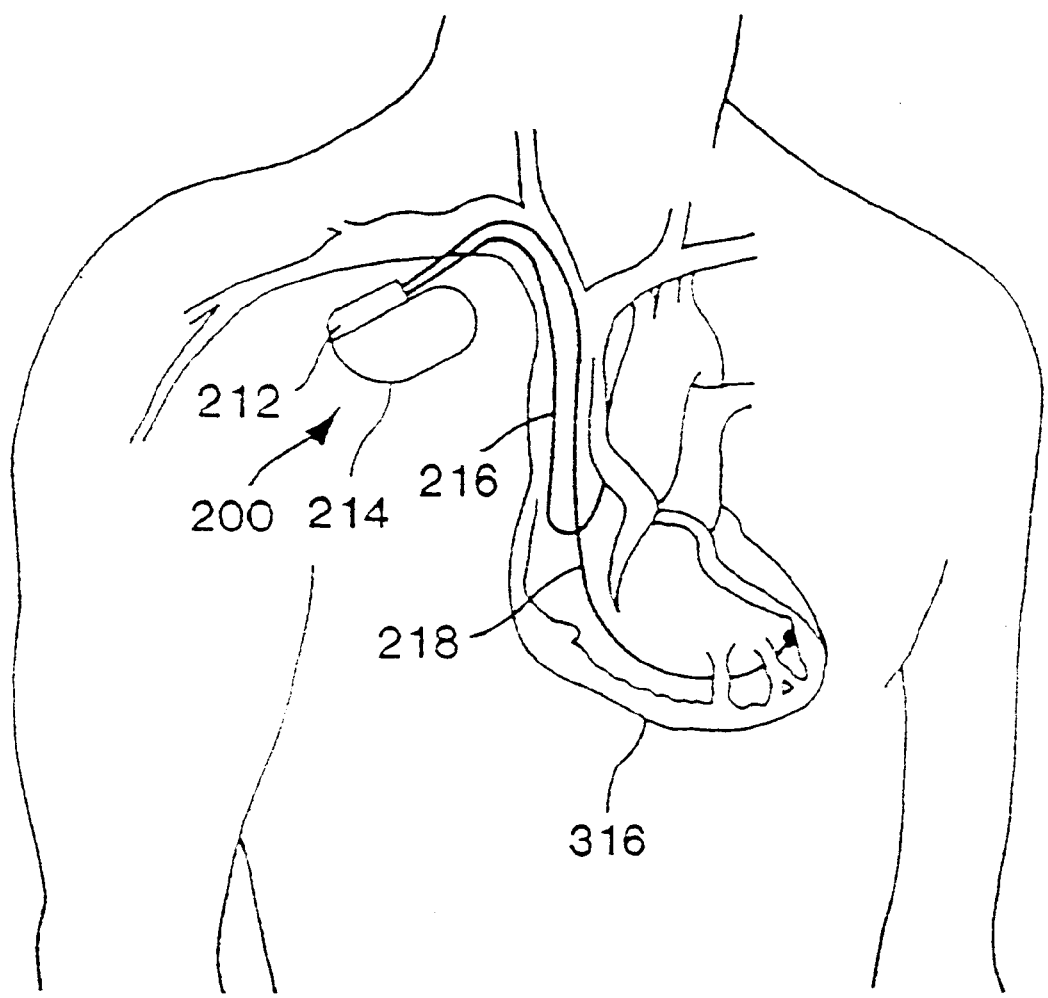
FIG. 2 is a simplified schematic view of an implantable medical device embodying the present invention.

FIG. 2 is a simplified schematic view of an implantable medical device 200 embodying the present invention, where at least one improved pacing and sensing lead 218 is attached to an hermetically sealed enclosure 214 and implanted near human heart 316. In the case where implanted medical device 200 is a pacemaker it includes at least one or both of pacing and sensing leads 216 and 218. Pacing and sensing leads 216 and 218 sense electrical signals attendant to the depolarization and re-polarization of the heart 316, and provide pacing pulses for causing depolarization of cardiac tissue in the vicinity of the distal ends thereof. Implantable medical device 200 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties.

Implantable medical device 200 may also be a PCD (Pacemaker-Cardioverter-Defibrillator) corresponding to any of the various commercially available implantable PCDs, with the substitution of pacing or sensing leads connector module 212 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 212.

Alternatively, implantable medical device 200 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 214 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with AID conversion of sampled EGM amplitude values. The particular electronic features and operations of the implantable medical device are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. The present invention may also be practiced in connection with multiple-chamber (e.g., dual-chamber) pacemakers.

Figure 3:
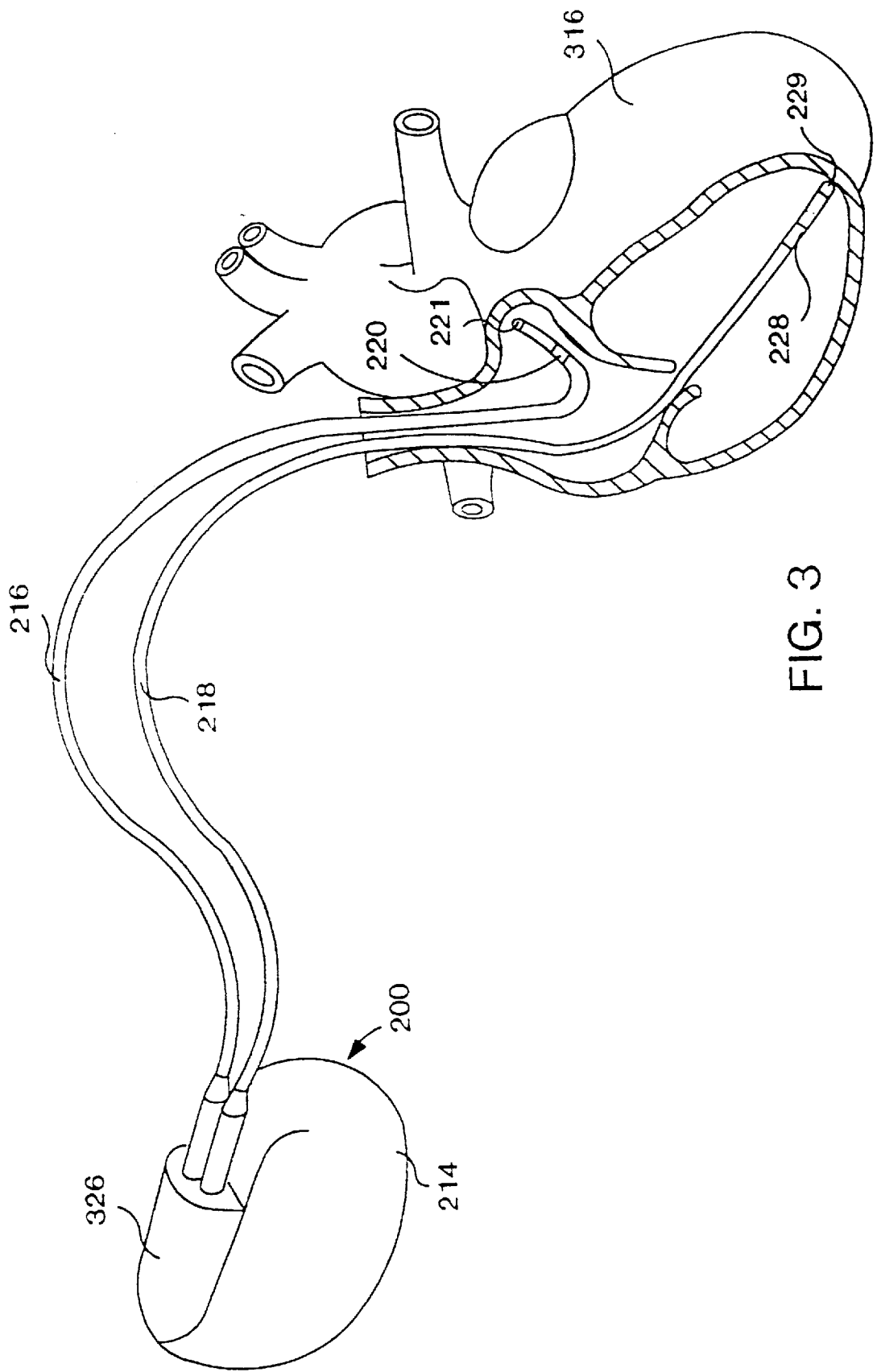
FIG. 3 depicts a connector module and hermetically sealed enclosure of an implantable medical device as they relate to a patient's heart.

FIG. 3 depicts connector module 212 and hermetically sealed enclosure 214 of implantable medical device or dual chamber pacemaker IPG 200 as they relate to a patient's heart 316. Atrial and ventricular pacing leads 216 and 218 extend from connector header module 212 to the right atrium and ventricle, respectively. Atrial electrodes 220 and 221 disposed at the distal end of the atrial pacing lead 216 are located in the right atrium. Ventricular electrodes 228 and 229 at the distal end of ventricular pacing lead 218 are located in the right ventricle.

Figure 4:
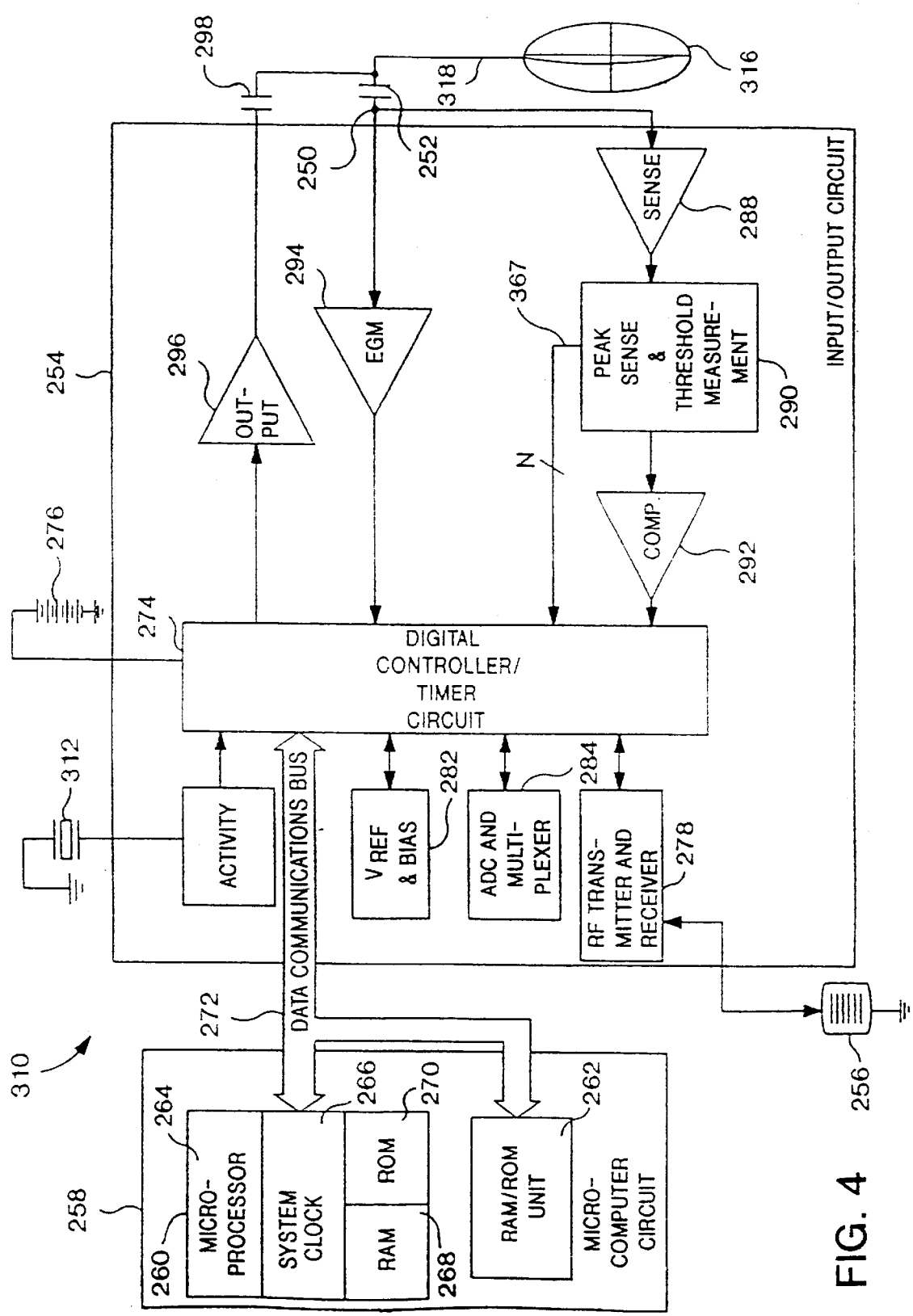
FIG. 4 shows a block diagram illustrating the constituent components of a pacemaker in accordance with the invention.

FIG. 4 shows a block diagram illustrating the constituent components of a pacemaker 310 in accordance with one embodiment of the present invention, where pacemaker 310 has a microprocessor-based architecture. The present invention may be utilized in conjunction with other implantable medical devices, however, such as cardioverters, defibrillators, cardiac assist systems, and the like, or in conjunction with other design architectures.

In the illustrative embodiment shown in FIG. 3, pacemaker 310 includes an activity sensor 312, which is preferably a piezoceramic accelerometer bonded to the hybrid circuit inside the pacemaker housing. Piezoceramic accelerometer sensor 312 provides a sensor output which varies as a function of a measured parameter that relates to the metabolic requirements of patient.

Pacemaker 310 of FIG. 3 is most preferably programmable by means of an external programming unit (not shown in the Figures). One such programmer suitable for the purposes of the present invention is the commercially available Medtronic Model 9790 programmer. The programmer is a microprocessor device which provides a series of encoded signals to pacemaker 310 by means of a programming head which transmits radio-frequency (RF) encoded signals to pacemaker 310 according to a telemetry system such as that described in U.S. Pat. No. 5,312,453 to Wyborny et al., the disclosure of which is hereby incorporated by reference herein in its entirety. It is to be understood, however, that the programming methodology disclosed in Wyborny et al. patent is identified herein for the illustrative purposes only, and that any programming methodology may be employed so long as the desired information is transmitted to and from the pacemaker. One of skill in the art may choose from any of a number of available programming techniques to accomplish this task.

Pacemaker 310 is schematically shown in FIG. 3 to be electrically coupled to a pacing lead 318 disposed in patient's heart 316. Lead 318 preferably includes an intracardiac electrode disposed at or near its distal end and positioned within the right ventricular (RV) or right atrial (RA) chamber of heart 316. Lead 318 may have unipolar or bipolar electrodes disposed thereon, as is well known in the art. Although an application of the present invention in the context of a single-chamber pacemaker is disclosed herein for illustrative purposes, it is to be understood that the present invention may equally well be applied in the context of a dual-chamber pacemakers or other implantable device.

Lead 318 is coupled to a node 250 in the circuitry of pacemaker 310 through input capacitor 252. In the presently disclosed embodiment, accelerometer 312 is attached to the hybrid circuit inside pacemaker 310, and is not shown explicitly in FIG. 3. The output from accelerometer 312 is coupled to input/output circuit 254. Input/output circuit 254 contains analog circuits for interfacing to heart 316, accelerometer 312, antenna 256, and circuits for the application of stimulating pulses to heart 316 to control its rate under control of software-implemented algorithms in microcomputer circuit 258.

Microcomputer circuit 258 preferably comprises on-board circuit 260 and off-board circuit 262. Circuit 258 may correspond to the microcomputer circuit disclosed in U.S. Pat. No. 5,312,453 to Shelton et al., the disclosure of which is hereby incorporated by reference herein in its entirety. On-board circuit 260 includes microprocessor 264, system clock circuit 266, and on-board RAM 268 and ROM 270. In the presently disclosed embodiment of the invention, off-board circuit 262 comprises a RAM/ROM unit. On-board circuit 260 and off-board circuit 262 are each coupled by a data communication bus 272 to a digital controller/timer circuit 274. Microcomputer circuit 258 may form a custom integrated circuit device augmented by standard RAM/ROM components.

The electrical components shown in FIG. 3 are powered by an appropriate implantable battery power source 276, in accordance with common practice in the art. For the sake of clarity, the coupling of battery power to the various components of pacemaker 310 is not shown in the Figures.

Antenna 256 is connected to input/output circuit 254 to permit uplink/downlink telemetry through RF transmitter and receiver unit 278. Unit 278 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. The particular programming and telemetry scheme chosen is not believed to be critical for purposes of practicing the present invention so long as entry and storage of values of rate-response parameters are permitted.

$V_{REF}$ and Bias circuit 282 generates a stable voltage reference and bias currents for the analog circuits of input/output circuit 254. Analog-to-digital converter (ADC) and multiplexer unit 284 digitizes analog signals and voltages to provide "real-time" telemetry intracardiac signals and battery end-of-life (EOL) replacement function.

Operating commands for controlling the timing of pacemaker 310 are coupled by data bus 272 to digital controller/timer circuit 274, where digital timers and counters establish the overall escape interval of the pacemaker as well as various refractory, blanking and other timing windows for controlling the operation of the peripheral components disposed within input/output circuit 254.

Digital controller/timer circuit 274 is preferably coupled to sensing circuitry, including sense amplifier 288, peak sense and threshold measurement unit 290 and comparator/threshold detector 292. Circuit 274 is further preferably coupled to electrogram (EGM) amplifier 294 for receiving amplified and processed signals sensed by an electrode disposed on lead 318. Sense amplifier 288 amplifies sensed electrical cardiac signals and provides an amplified signal to peak sense and threshold measurement circuitry 290, which in turn provides an indication of peak sensed voltages and measured sense amplifier threshold voltages on multiple conductor signal path 367 to digital controller/timer circuit 274. An amplified sense amplifier signal is then provided to comparator/threshold detector 292. Sense amplifier 288 may correspond to that disclosed in U.S. Pat. No. 4,379,459 to Stein, which is hereby incorporated by reference herein in its entirety.

The electrogram signal provided by EGM amplifier 294 is employed when the implanted device is being interrogated by an external programmer (not shown) to transmit by uplink telemetric means a representation of an analog electrogram of the patient's electrical heart activity. See, for example, U.S. Pat. No. 4,556,063 to Thompson et al., hereby incorporated by reference herein in its entirety. Output pulse generator 296 provides pacing stimuli to patient's heart 316 through coupling capacitor 298 in response to a pacing trigger signal provided by digital controller/timer circuit 274 each time the escape interval times out, an externally transmitted pacing command is received, or in response to other stored commands as is well known in the pacing art. Output amplifier 296 may correspond generally to the output amplifier disclosed in U.S. Pat. No. 4,476,868 to Thompson, also incorporated by reference herein in its entirety.

While specific embodiments of input amplifier 288, output amplifier 296 and EGM amplifier 294 have been identified herein, this is done for the purposes of illustration only. The specific embodiments of such circuits are not critical to practicing the present invention so long as the circuits provide means for generating a stimulating pulse and are capable of providing digital controller/timer circuit 274 with signals indicative of natural or stimulated contractions of the heart.

Figure 5:
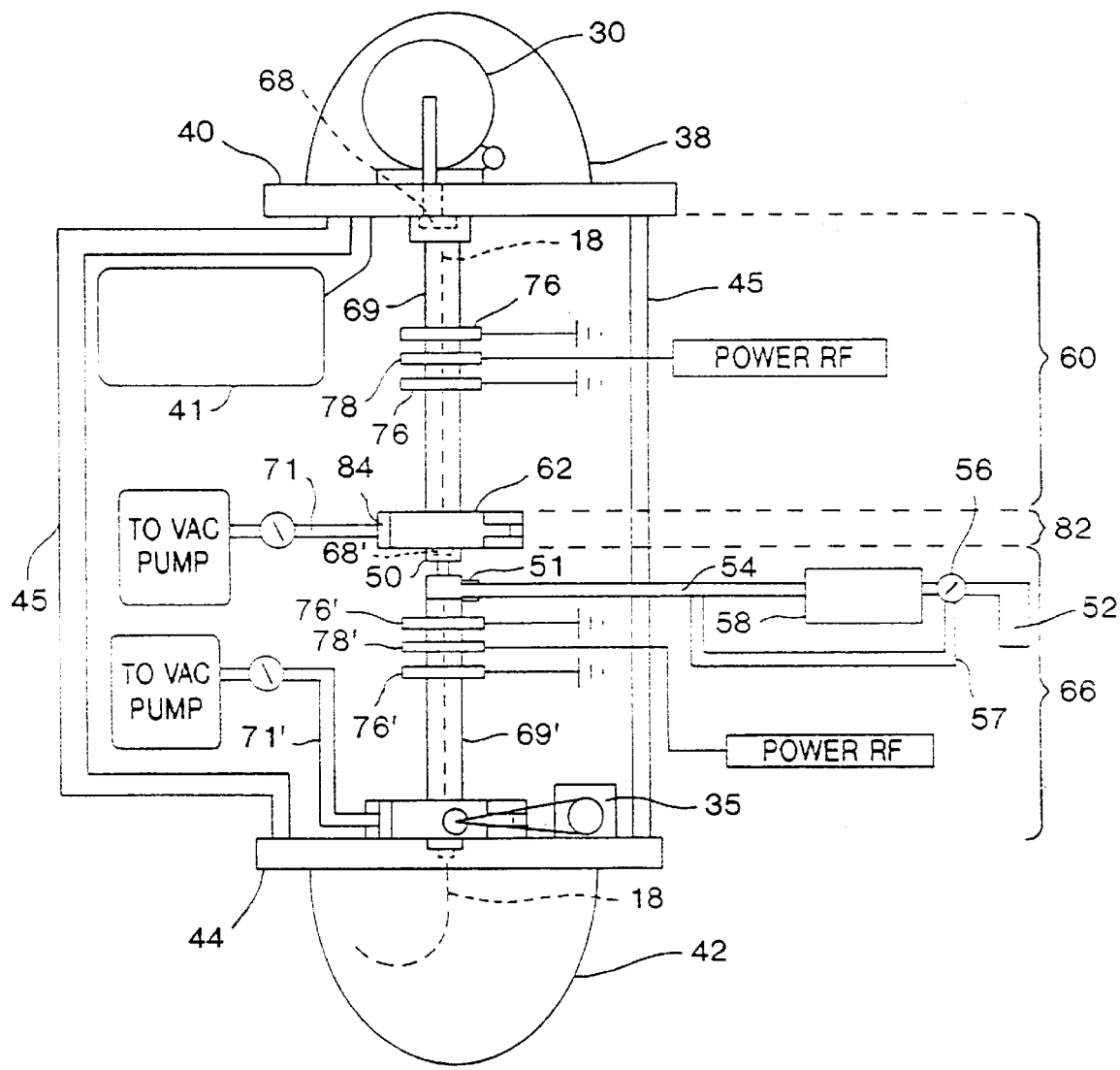
FIG. 5 depicts a continuous process plasma reactor that allows optional plasma discharge pretreatment of the OD surface of the tubing followed by depositing a monomer to form surface texture on the OD surface of the tubing.

FIG. 5 shows a plasma discharge apparatus 10 useful for making textured tubing according to the invention. The pretreatment zone 60 is optional, and when present contains the first plasma that the tubing 18 passes through after coming off of reel 30. The top of this section of the apparatus seals against the underside of the top plate assembly 40, which is connected to the support tower 45. The bottom of this section seals against the "transition zone" block 62. In the pretreatment zone 60, the tubing 18 receives an inert gas plasma pretreatment on its outer surface.

Upon entry into pretreatment or glow discharge zone 60, the tubing may pass through a close fitting orifice 68, which generally should have a diameter equal to the tubing nominal OD plus 0.001 in ±0.0001 in. This diameter may vary depending on the type of tubing and type of treatment or coating to be performed. For tubing 0.054 inch OD the orifice should be drilled to about 0.055 inches. This size may later be adjusted to achieve precise pressure differentials. The orifice serves to a) prevent the glow discharge from spreading into the upper bell jar 38, b) allow different pressures or types of gasses to be maintained in the upper chamber 38 and pre-treatment zone 60, c) guide the tubing 18 down the center of the pretreatment zone 60, and d) allow a small gas flow from the upper chamber 38 to the glass tube 69 below where a vacuum exhaust line 71 may be arranged to carry away the flow.

The pretreatment zone 60 typically includes a section of glass tube 69 which is commonly available as a sanitary glass tube. The length of the glass tube 69 may typically be from about 3 to about 18 inches in length, more preferably from about 6 to about 12 inches in length, and most preferably from about 6 to about 10 inches in length. The glass tube 69 should be capable of forming a vacuum seal with each end of the tube butting up against an O-ring (not shown). Provision is made to allow for entry of gases below the orifice 68 and above the end of the glass tube 69.

Preferably, the glass tube 69 has a diameter sufficiently large so that the pretreatment of the OD surface is substantially uniform. More preferably, the diameter is about 0.5 inches to about 1.5 inches and most preferably, about 1.5 inches. When the OD of the glass tube 69 is less than about 0.5 inches, the tubing 18 must be substantially centered in order to maintain a uniform glow discharge at lower gas pressures. Thus, a larger glass tube 69 tolerates more misalignment and provides a more uniform discharge around the tubing 18.

A plurality of circular, torus shaped ground electrodes 76, preferably two, and an RF powered electrode 78 are dimensioned to suit the diameter and length of the glass tube 69. A PTFE insulator support bar 46 may be included to hold them in place. The two ground electrodes 76 may be connected by a common ground strap (not shown).

As the tubing 18 passes through the pre-treatment zone 60, a glow discharge is produced by the inert gas by reactance coupling utilizing power provided by the radio frequency power source, shown as electrodes 76 and 78. Under plasma discharge conditions, the inert gas treatment activates the polymeric surface of the tubing in preparation for application of the monomer. While not intending to be bound by any particular theory, it is believed that pretreatment by inert gas plasma causes the polymeric surface of the tubing 18 to crosslink and form a population of free radical sites.

Transition zone 82 serves as a connection between the pretreatment zone 60 and the surface texturing zone 66. Preferably, the transition zone 82 a) is capable of forming a vacuum seal to the lower end of the pre-treatment glass tube 69, b) connects with the compression fitting 50 of the monomer deposition zone 66 below it, c) provides a vacuum port 84 which connects to an automatic throttle valve pressure controller (this allows gas flow which enters through or below the orifice 68 at the top of the pre-treatment zone 60 to be drawn off below the pre-treatment zone), and d) provides a rigid connection to the upper end of the monomer deposition zone 66 in order to minimize or prevent any relative motion between the top and bottom compression fittings 50 of the monomer deposition zone 66.

The surface texturing zone 66 (see FIG. 6 in particular) performs the monomer deposition that produces the surface texture on the OD surface of the tubing 18 as it moves through the surface texturing zone 66. In the surface texturing zone 66, a monomer is delivered as a vapor to the glow discharge zone. The surface texturing zone 66 preferably includes an electrode and glass tube configuration similar to that used in the pretreatment zone 60. The pretreatment on the outer surface tubing 18 in the pretreatment zone 60 is preferably performed prior to entry into the glass tube 69'.

Upon entry into surface texturing zone 66, the glass tube 69' may pass through a close fitting orifice 68'. Typically a radio frequency plasma excitation (13.56 Mhz) source is used to excite the plasma, which requires that glass tube 69' have a length of at least about 16 inches. The length of the glass tube 69' is preferably about 6 inches to about 12 inches if using capacitive electrodes.

Electrode configuration may vary. However, the circular disc or torus shaped electrodes 76' and 78' are dimensioned to suit the diameter and length of the OD tube 69', as described with respect to the pre-treatment zone 60. Also, a PTFE insulator support bar may be included, and the two ground electrodes 76' may be connected by a common ground strap. In other words, the configuration may be similar to that in the pretreatment zone 60, described above.

In addition to an electrode configuration and a glass tube, the surface texturing zone 66 further includes a monomer source 55. The monomer source 55 typically includes a monomer reservoir 52, a mass flow controller 58, a monomer conduit 54, a monomer inlet 51, and a vacuum bypass line 57. The monomer, typically liquid or gas, is held in the monomer reservoir 52. A monomer suitable for use in the present invention is one that can be vaporized.

The monomer is discharged through the monomer conduit 54 to the monomer inlet 51, where the monomer enters the glass tube 69' of the monomer deposition zone 66. Preferably, the monomer conduit 54 is heated to a temperature approximately equal to or greater than the boiling point of the monomer so that the monomer can be introduced in the monomer deposition chamber 66 without condensation as a monomer vapor. For example, when the monomer is HMDSO, the monomer conduit 54 is at a temperature of about 30° C. or greater.

The monomer source 55 may optionally include a bypass valve 56 around the monomer mass flow controller 58 for removal of monomer reservoir headspace gases prior to the flow of the monomer vapor through the monomer mass flow controller.

The plasma discharge apparatus 10 is enclosed within a partially evacuated (i.e., low pressure) environment. In the pretreatment zone 60, the partially evacuated environment may contain an inert gas, preferably an inert gas selected from the group of nitrogen, helium, neon, argon, and mixtures thereof. More preferably, the gas is argon. The gas is at a suitable pressure for discharge such as 0.1 Torr. In the surface texturing zone 66, the evacuated environment may contain the monomer, typically in the form of a vapor.

In the pretreatment zone 60, the RF powered electrode 78 is preferably operated in a continuous mode. For example, it was found that a power level of about 20 watts to about 300 watts at a continuous mode was effective to pretreat the tubing. In the surface texturing zone 66, the RF powered electrode 78' is also preferably operated in a continuous mode. For example, it was found that a power level of about 20 watts to about 200 watts, more preferably about 40 watts to about 90 watts, operated at a continuous mode, produced a monomer discharge effective to texture the OD surface of the tubing.

Figure 6:
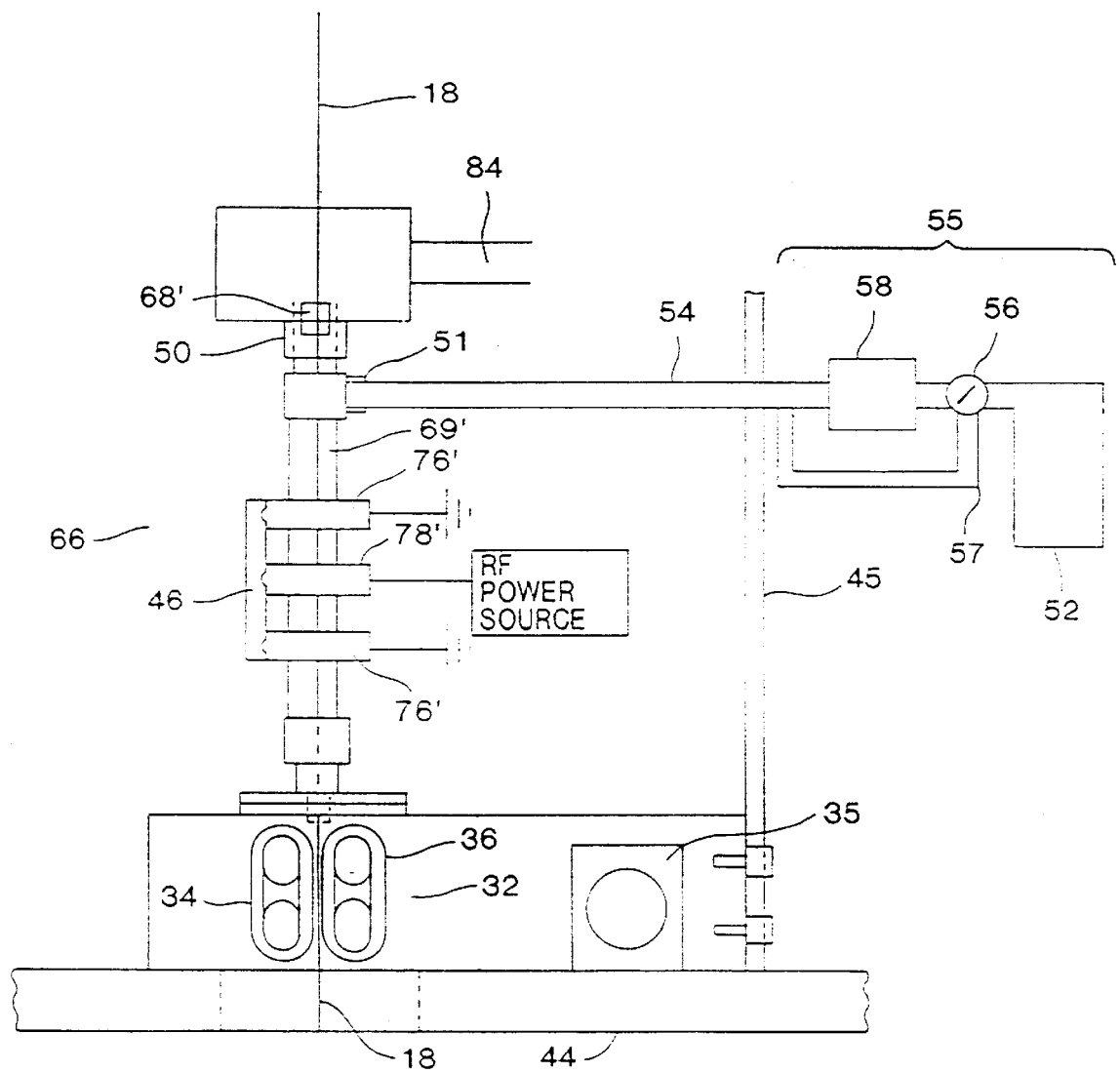
FIG. 6 is a detailed schematic of the tubing drive and tension monitoring system of the plasma reactor of FIG. 5.

The tubing 18 moves through the bore of the glass tubes 69 and 69' as by being pulled therethrough, thus passing the tubing through each of the discharge zones which exist between the two sets of electrodes. The tubing 18 is held on a spool 30 at the top (or inlet end) of the apparatus from which it is pulled by a means such as a tubing transport track drive 32 which is positioned at the bottom (or outlet end) of the apparatus (FIG. 6). The track drive 32 may include a pair of electrically driven controlled speed drive belts 34 and 36. Other arrangements for pulling the tubing through the apparatus will be apparent to those familiar with this art. Continuous tension is applied to the tubing, for example about 5 to about 100 grams, more preferably about 15 to about 55 grams, to provide controlled deposition of surface texture. The line speed to produce texture on the OD surface of the tubing in the surface texturing zone is preferably about 10 to about 100 inches per minute, more preferably about 20 to about 40 inches per minute.

In a batch process, wherein surface texture is formed on a elastomeric substrate, typically a planar elastomeric substrate, the substrate is preferably subjected to plasma deposition using continuous RF power of about 30 Watts to about 200 Watts, for about 1 minute to about 30 minutes, at pressures of about 50 mTorr to about 2 Torr, using gas and monomer flow rates of about 1 to about 40 sccm/minute. More preferably, the planar substrate is prestretched prior to plasma deposition, for example a sheet of silicone can be slightly stretched or more tightly stretched, up to several times its original size, prior to plasma deposition of surface texture. Alternatively, surface texture can be deposited onto an unstretched elastomeric surface, planar or nonplanar, in a batch process according to the invention.

Returning to the continuous plasma deposition process as shown in FIG. 5, the spool 30 and the supply of tubing 18 it carries are maintained within a sealed environment by means of an upper bell jar 38 or the like which seals against an upper plate 40. Likewise, the treated tubing which is collected at the bottom of the apparatus is contained within a sealed environment provided by lower bell jar arrangement 42 which seals against bottom plate 44. Other means for providing sealed chamber arrangements will be readily apparent to those familiar with this art.

Figure 7:
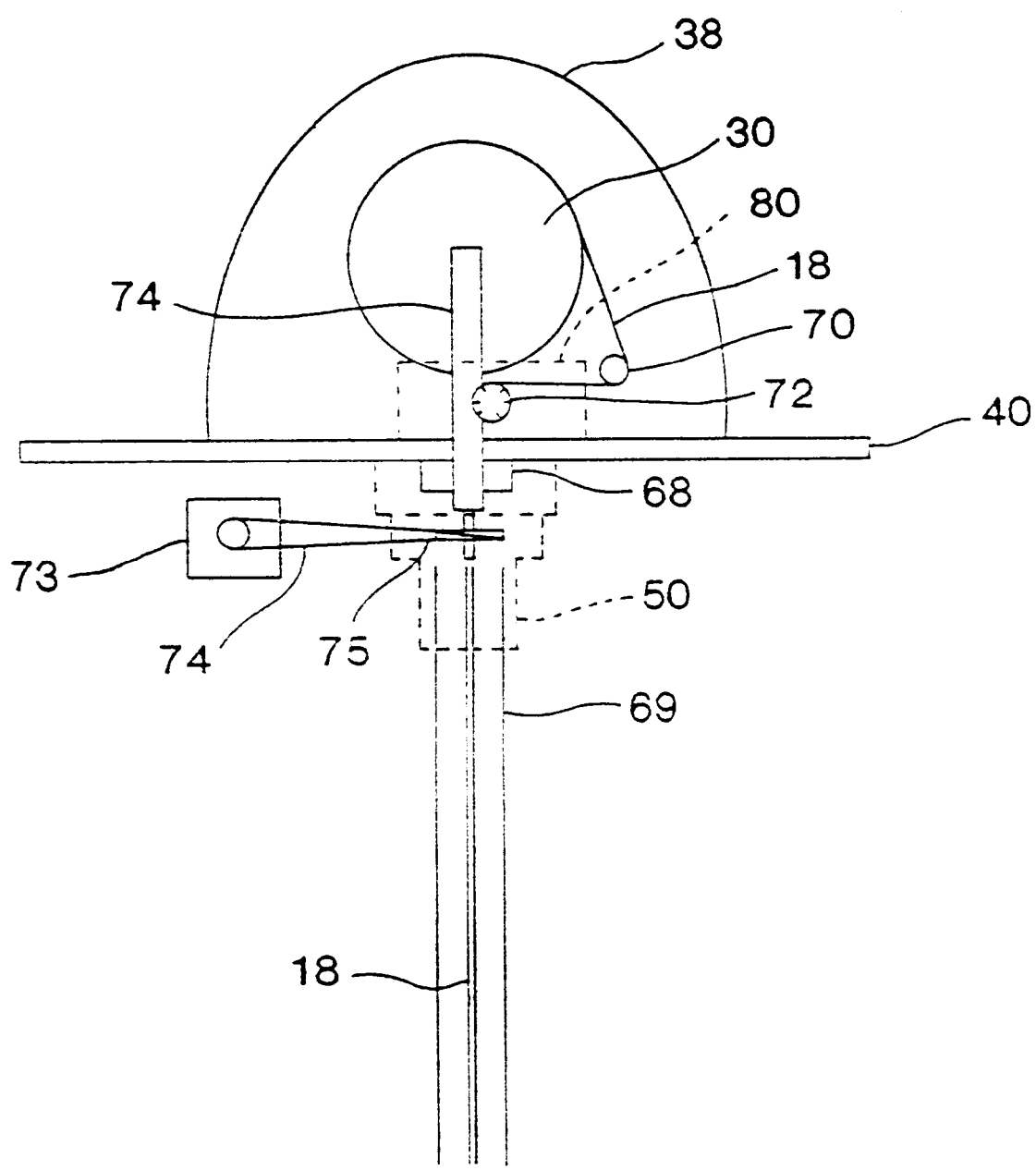
FIG. 7 is a detailed schematic of the surface texturing zone of the plasma reactor of FIG. 5.

Together FIGS. 6 and 7 depict the tubing drive and tension monitoring system for the plasma rector in detail. An optical encoder 80 (i.e., a laser pulse counting diode) is electrically connected to the lower drive motor 35 to control the tubing speed, and a load cell assembly 72 is interlocked to an upper drive motor 73 to control tension. Tubing 18 is drawn from tubing spool 30 around the change of direction pulley 70 and through drive feedthrough 74, which is evacuated during plasma deposition. Drive feedthrough 74 also provides physical support for tubing spool 30. When the transport speed of the lower motor 35 is established, the upper motor 73 increases or decreases its speed to maintain the proper tension on the tubing, via drive belt 79, which is connected to drive pulley 75 which, in turn, drives the tubing spool 30. Line speed can be monitored using a laser directed through slots cut into the load cell assembly 72.

The gas-environment is provided by evacuating upper and lower bell jars 38 and 42, respectively, by means of a vacuum pump connected to outlet arrangement (not shown). Because glass tube 69 (69') is in sealed communication with both 38 and 42 the entire system is evacuated in this manner. Other chamber designs may be used. The selected discharge gas, such as argon in this instance, is introduced to the system through inlet arrangement 41 to a pressure such as 0.1 Torr.

While textured surfaces and surface modification methods in accordance with the invention have been described hereinabove, the following non-limiting examples will further illustrate the invention.

EXAMPLES

Example I

Plasma Deposition of Siloxane to Create Texture on Outer Diameter (OD) Surface of Silicone Tubing Materials and equipment.

Silicone tubing (single lumen, ID 0.057 inches, OD 0.079 inches) was obtained from Specialty Silicone Fabricators, Inc (Paso Robles, Calif.). Smaller diameter silicone tubing (ID 0.033 inches, OD 0.047 inches) was also treated in a separate experiment. The custom-built plasma reactor contained an outer diameter treatment zone (OD zone) followed by an inner diameter treatment zone (upper bell jar) and a lower bell jar. The ID zone (upper bell jar) was superfluous, however, since plasma monomers were not deposited on the ID surface of the tubing in this experiment.

The reactant monomer hexamethyldisiloxane (HMDSO) was obtained from Aldrich Chemical Company, Milwaukee, Wis.

Plasma deposition.

The plasma reactor was operated in manual mode. Operating parameters were: tubing tension, 25 g; line speed, 30 inches/minute; upper orifice diameter, 0.093 inches; ID upper bell jar pressure, 100 mT; ID upper bell jar gas, argon; ID upper bell jar argon flow, 2.00 sccm; ID upper bell jar glass, oversized; glass tube, 10 inch length; ID upper bell jar electrode, none; ID zone power, none; ID upper bell jar vapor source readout, 37.317; ID upper bell jar vapor, none; ID upper bell jar vapor flow, 0.0 sccm; OD zone diffuser, polyetheretherketone (PEEK) $\frac{1}{16}$ inch slots; OD zone pressure, 100 mT; OD zone co-gas, argon; OD zone argon flow, 9.00 sccm (sccm: standard cubic centimeters); OD zone vapor source readout, 38.50 T; OD zone vapor, HMDSO; OD zone vapor flow, 0.2 sccm; OD zone glass size, 1½ inch×16 inch; OD zone electrode; electrode model DG-300; OD zone power, radio frequency model RF5S 13.56 Mhz, 50 watts, continuous (not pulsed); OD zone RF cable length, standard; manifold pressure, 39.4 mT; lower drive block, "Bear Paw", 0.892 drive roller; lower bell jar gas, argon; lower bell jar pressure, 100 mT; lower bell jar gas flow rate; 2.0 sccm.

Tubing was unbagged on a clean benchtop and spliced to a length of 525 feet; then run through a solvent wipe cleaner at 55 pounds per square inch (psi). The vacuum fittings were loosened to load the tubing. The vacuum pump was then started with all valves completely open and all flows off, and allowed to draw a vacuum for about four hours. Gas and vapor flows were then initiated and allowed to equilibrate. When all zones were at the predetermined pressures, the reaction was begun by turning on the RF power, starting the tubing drive, and moving the tubing through the reactor. The process continued for 4 hours, 9 minutes, yielding over 523 feet of textured tubing. The reaction proceeded without difficulty except that two of the splices caused tubing tension to rise transiently to 50 g. The splices were then cut out of the textured silicone tubing, and the tubing was bagged in six sections ranging in length from 67 feet to 100 feet for use in biocompatibility testing as long term implants in rats (Example IV); a ten foot length of tubing was retained for further analysis.

Analysis of textured silicone tubing.

Figure 8A:
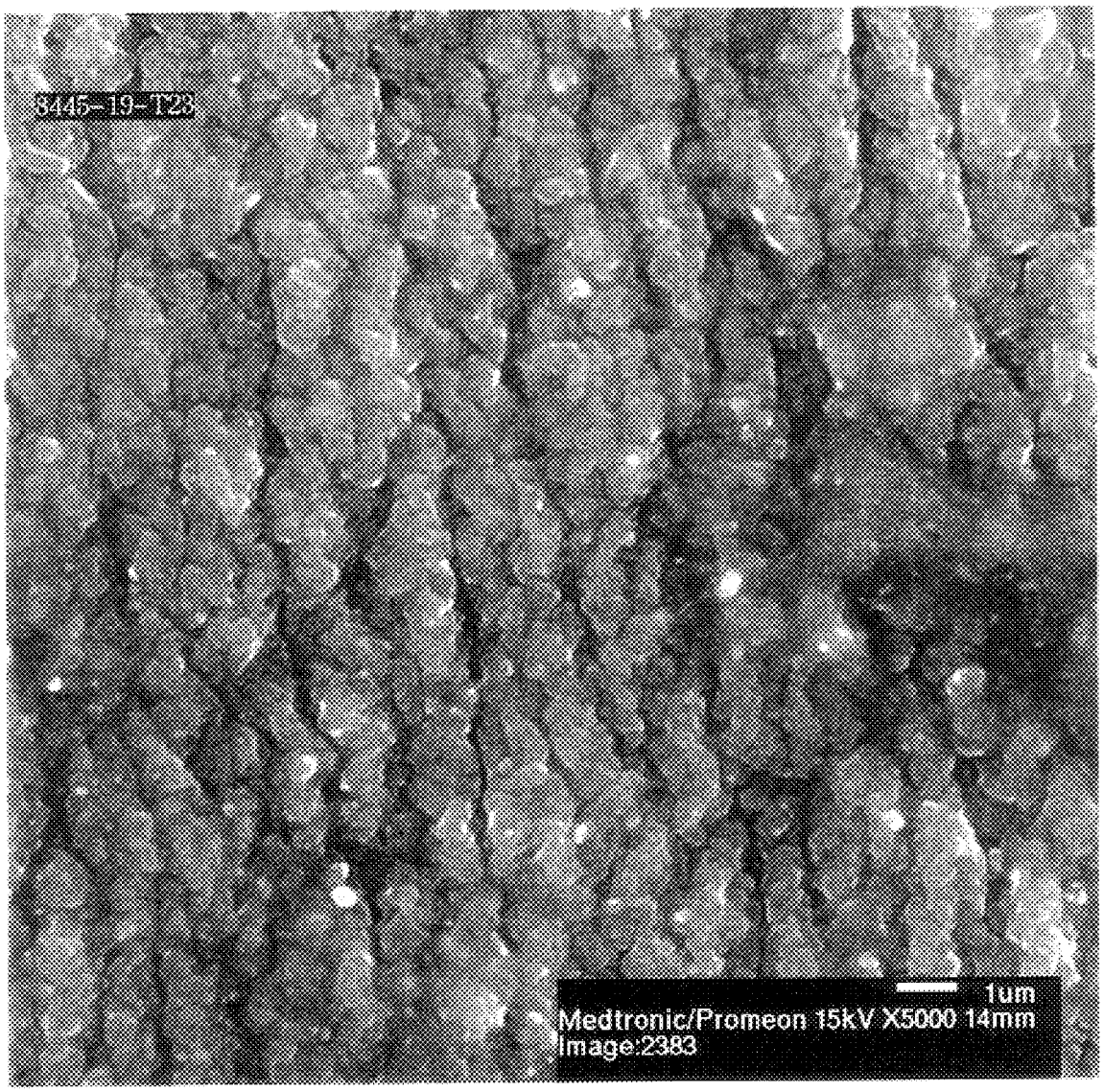
FIGS. 8A–8K show photomicrographs of silicone tubing having a textured surface according to the invention, the tubing positioned such that the longitudinal axis is left to right in the photomicrographs: (a) scanning electron microscopy (SEM) photomicrographs (5000×) showing nodular ridges; (b) SEM photomicrograph (15,000×) of a cross-section of textured tubing; (c) atomic force microscope (AFM) image of the tubing surface; (d) roughness analysis performed on a selected field within AMF image (c); (e) AFM cross-sectional scope trace of textured silicone tubing surface showing ridge-like features; (f) SEM photomicrograph (1000×) showing a region of relatively consistent "hills and valleys"; (g) SEM photomicrograph (1000×) showing a region with non-homogenous surface features; (h)–(k) ESEM photomicrographs (h:1000×; i:5000×; j:8000×; k:10,000×) of silicone tubing having a textured surface according to the invention.
Figure 8B:
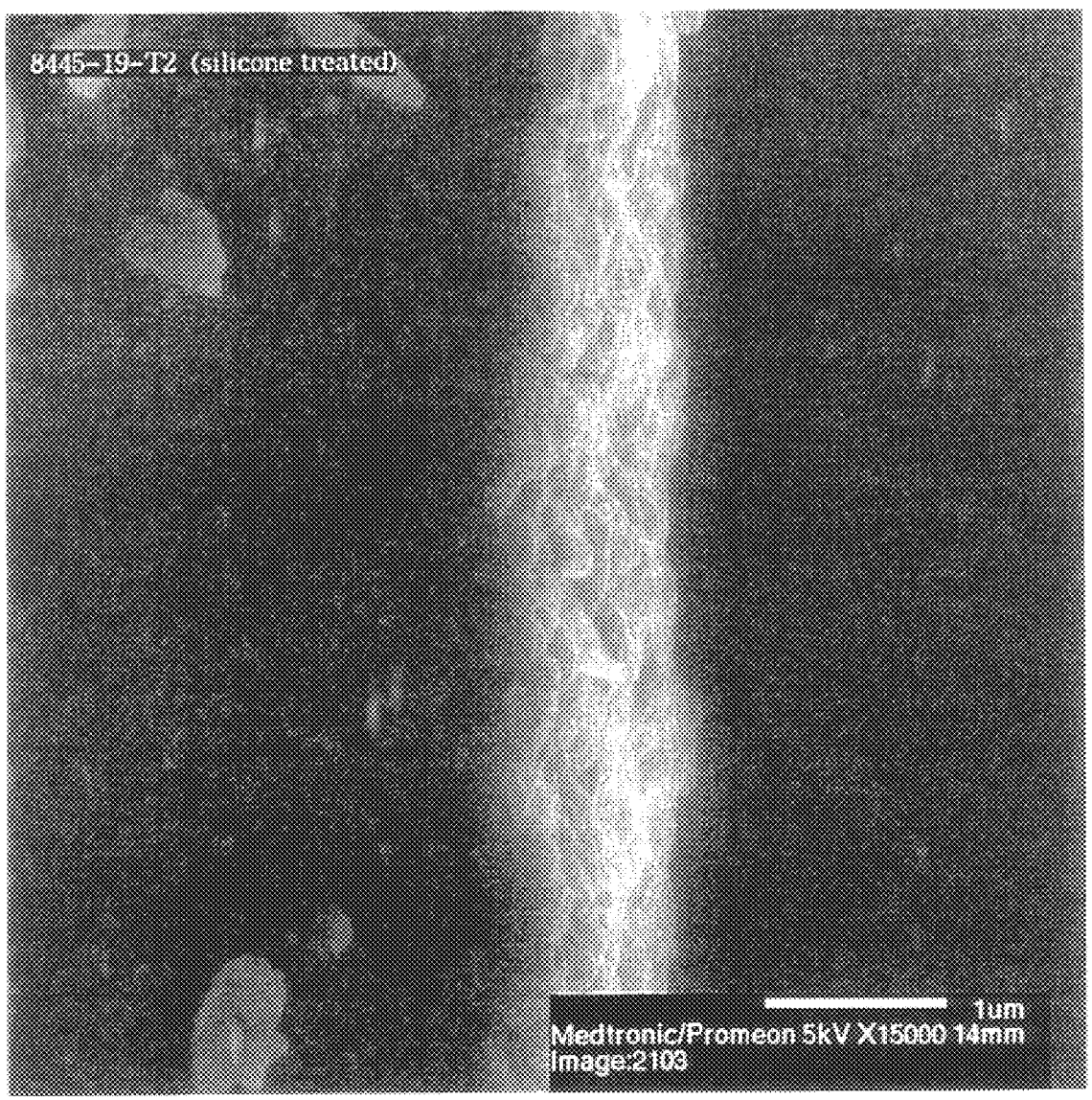
Figure 8C:
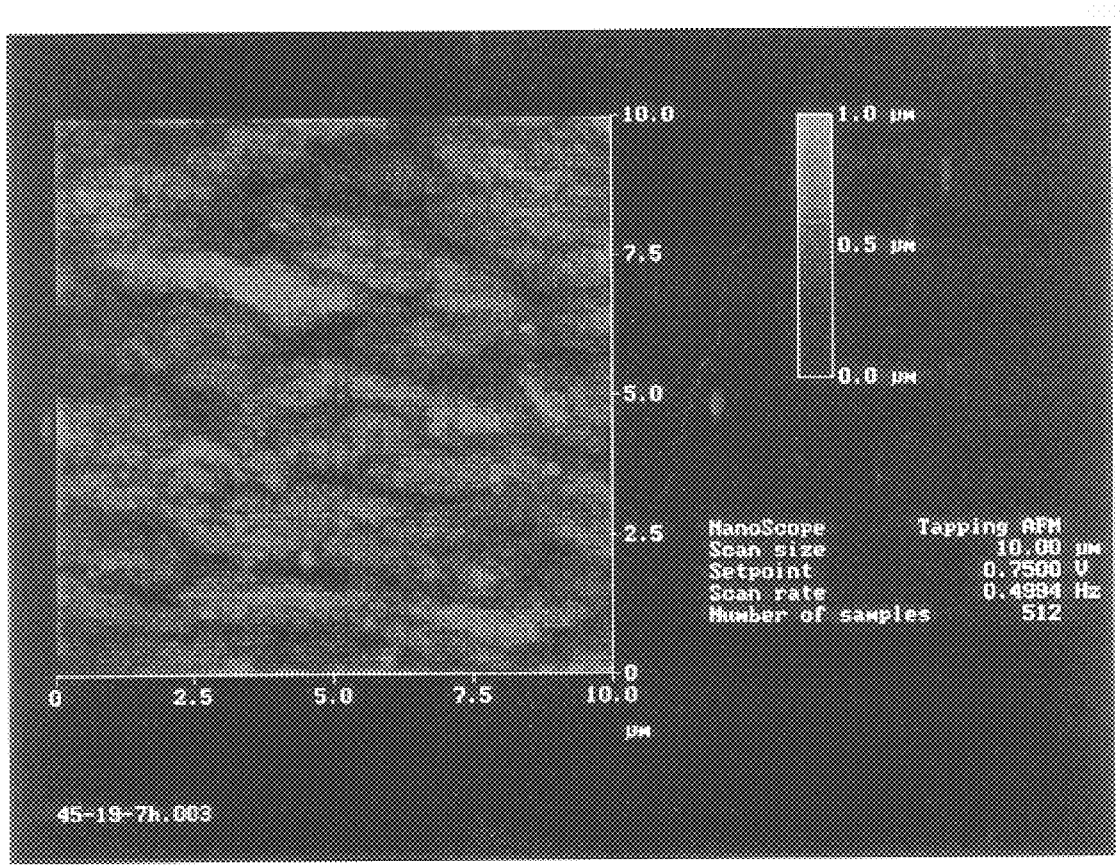
Figure 8D:
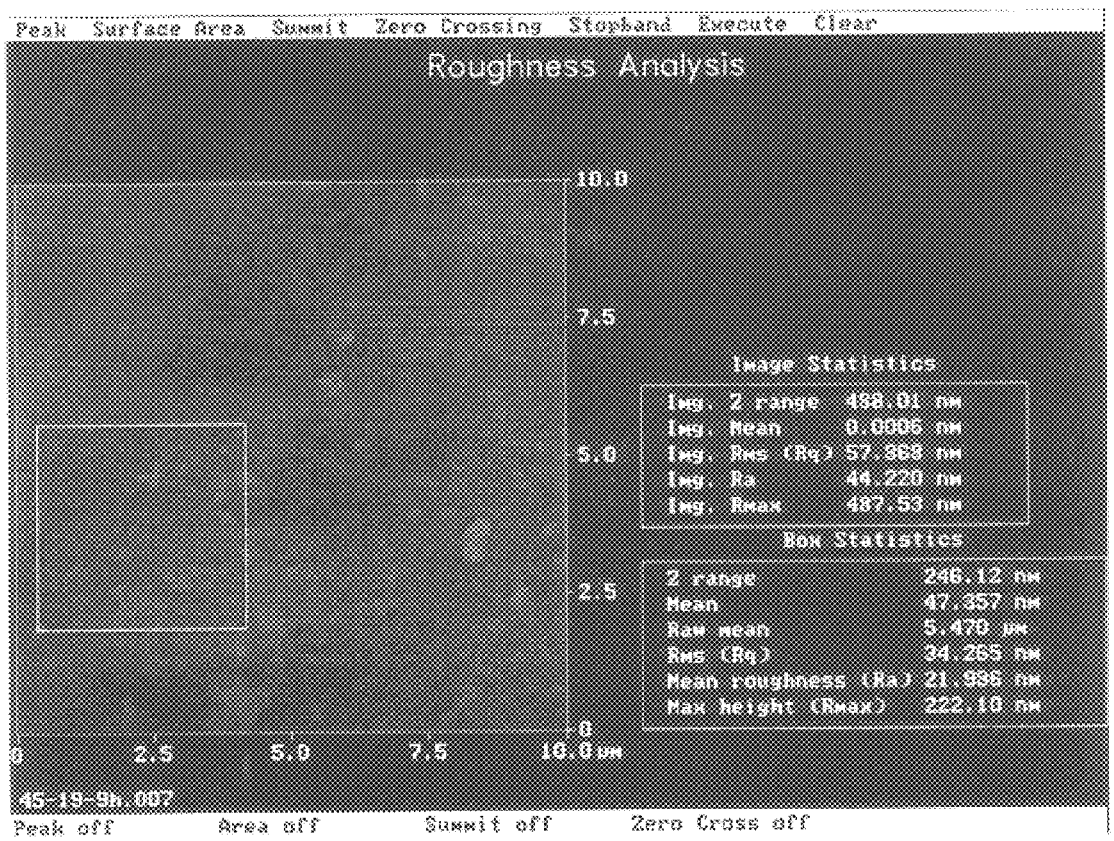
Figure 8E:
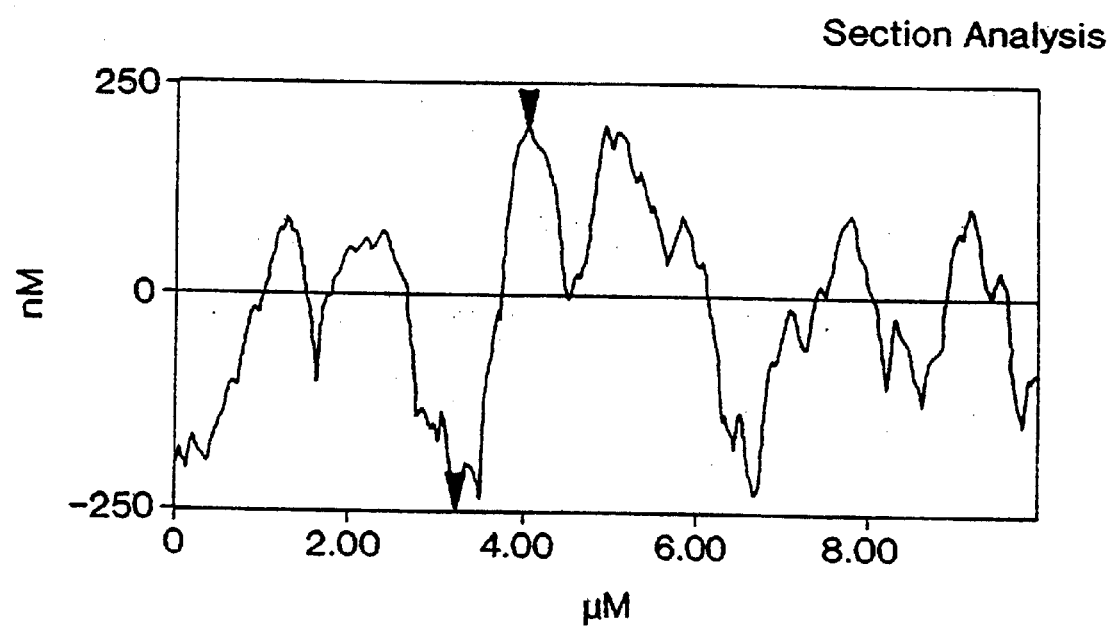

Cleaned and sterilized samples were evaluated by optical, scanning electron, and atomic force microscopy. Sections of tubing were examined optically under a microscope at 650× and representative photographs were taken (not shown). The typical nodular surface perpendicular to the tubing axis and to the stretched direction was noted. Samples from this deposition and untreated silicone tubing were also analyzed with atomic force microscopy (AFM). Atomic force microscopy was performed at the University of Minnesota at the CIE Characterization Facility. Treated samples were analyzed using a NanoScope employed in the tapping mode. The scanned area was 10 nm×10 nm and the scan rate was 0.4994 Hz with 512 samples accumulated (FIGS. 8c and 8d). AFM provides a height image and a section analysis of a slice of each sample surface. A section analysis is a topographical trace, along a line, of the sample surface. The trace of the untreated tubing showed that the surface was relatively smooth, having a root mean squared roughness of 39.1 nanometers. The siloxane plasma treated surface was more highly textured (FIG. 8e), having a root mean squared roughness of 159.3 nanometers. The surface consisted of a series of nodular ridges. The peak to valley vertical distance of the cross-section was measured to be about 450 nanometers. The spacing between the ridges was measured to be about 1 to 2 microns.

Figure 8F:
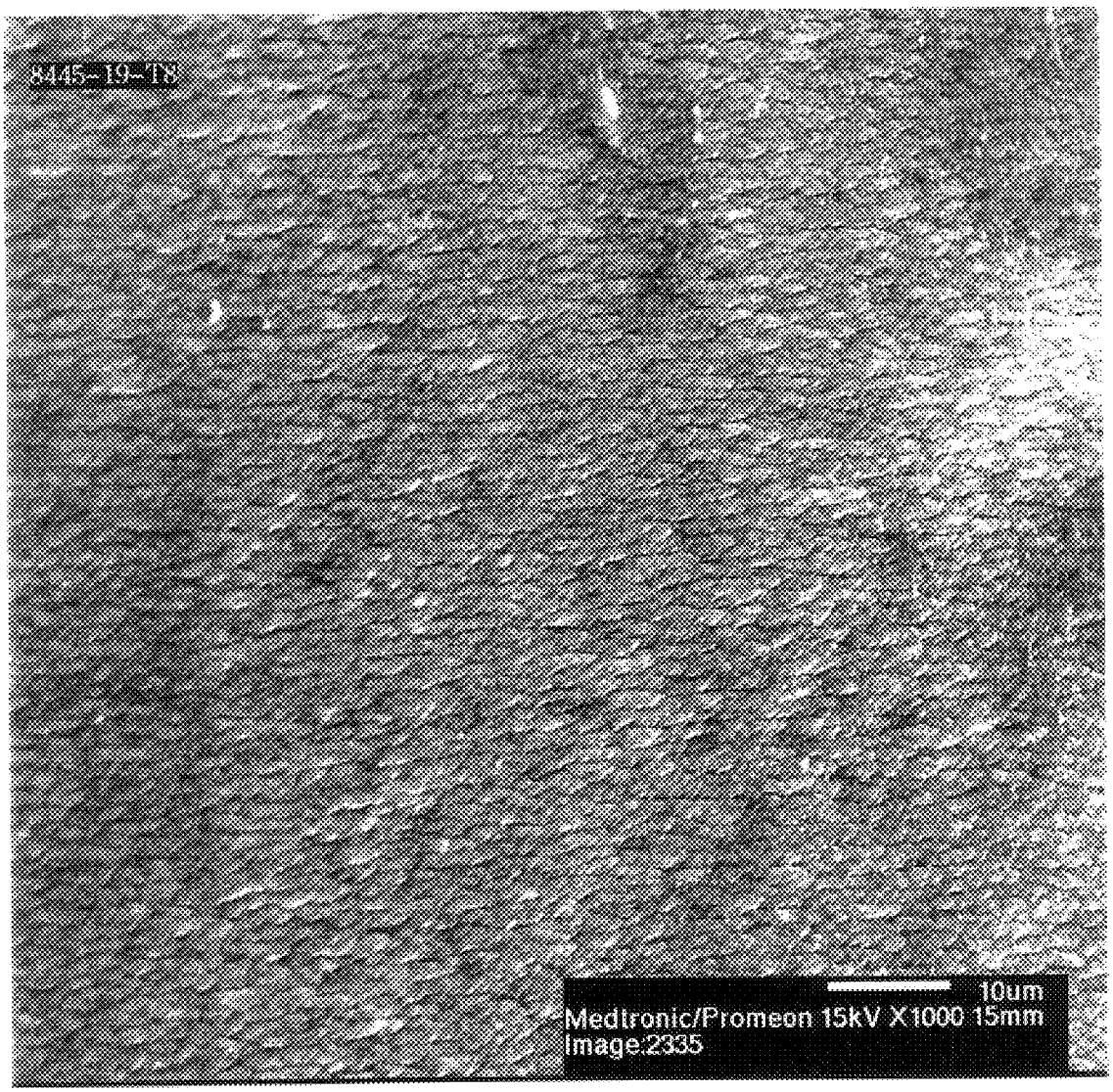
Figure 8G:
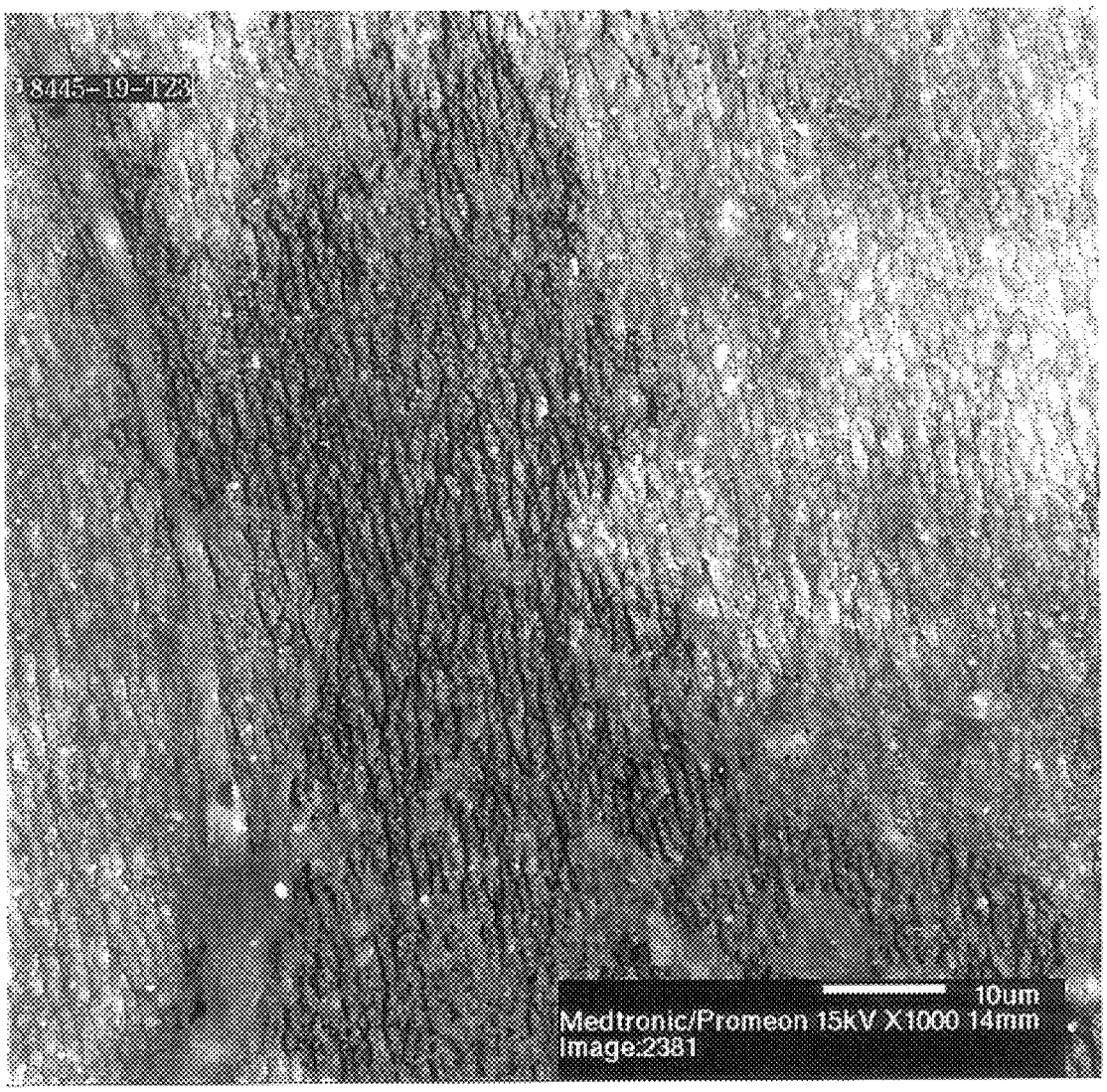
Figure 8H:
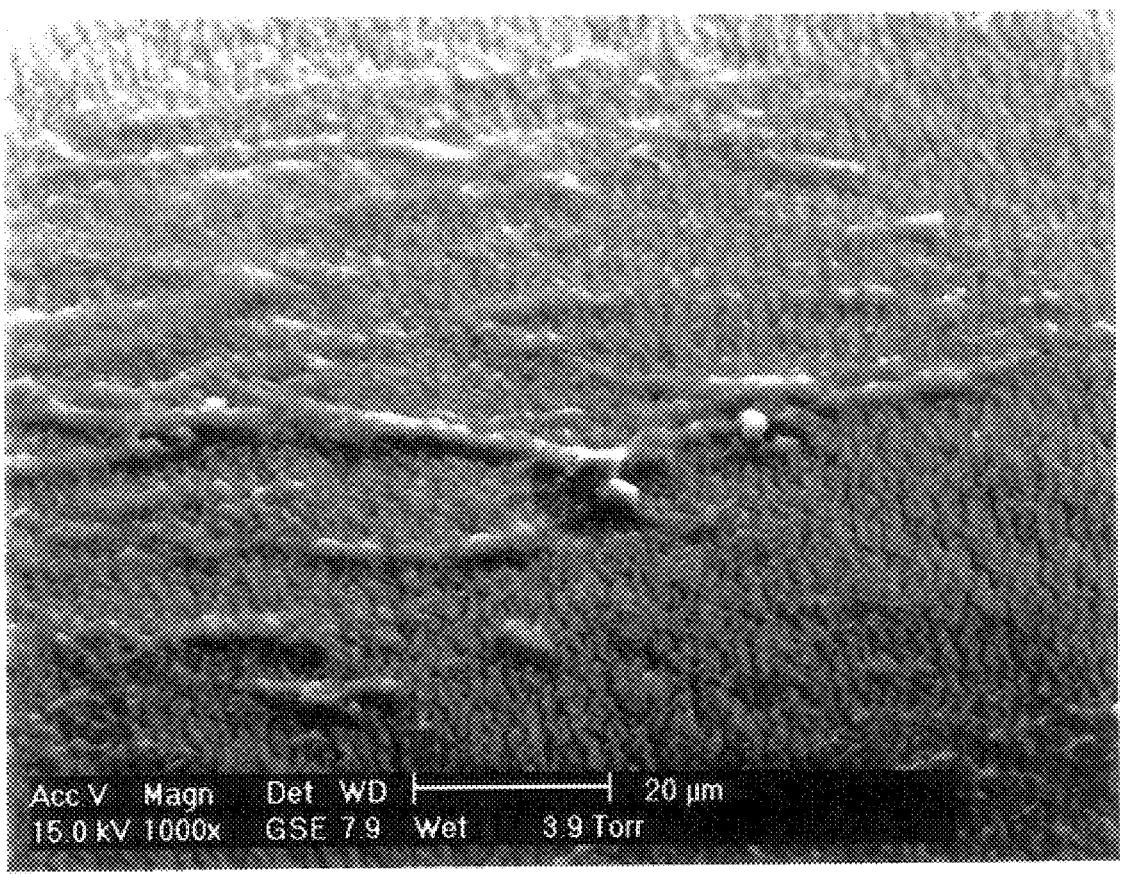
Figure 8I:
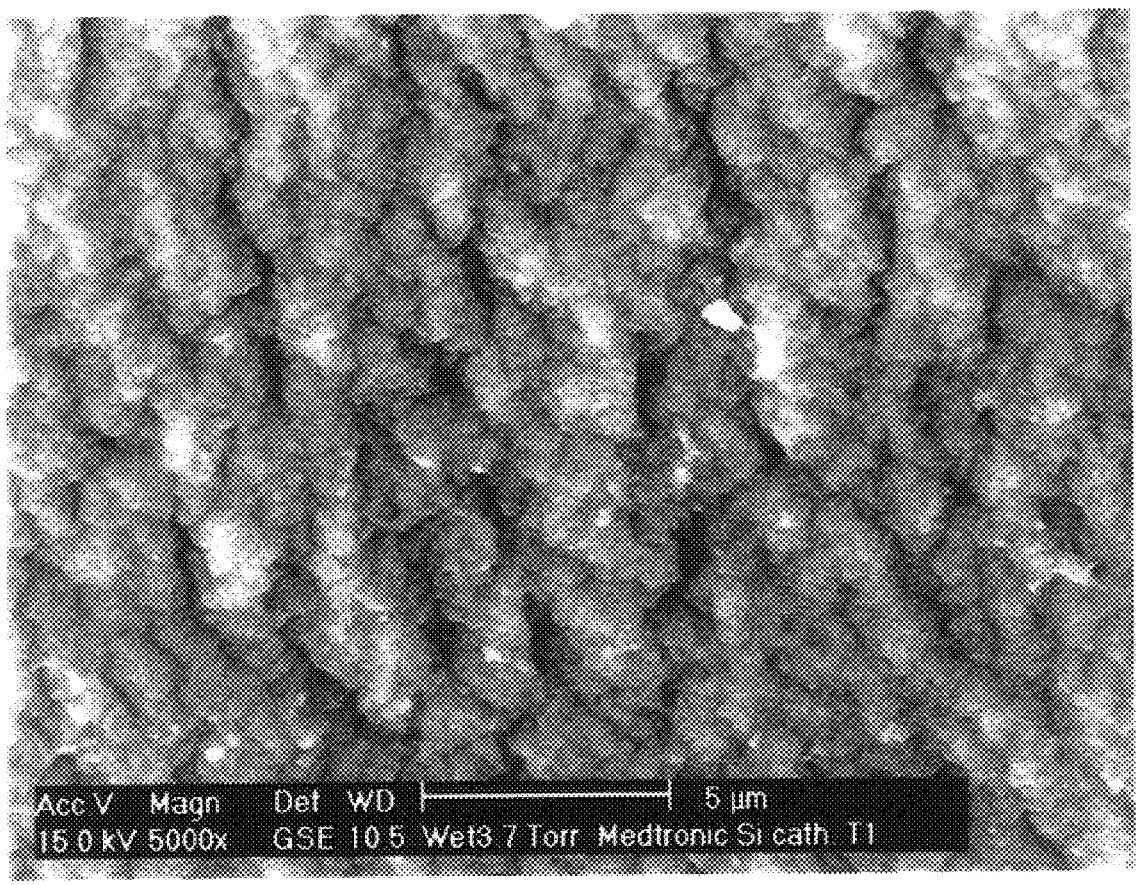
Figure 8J:
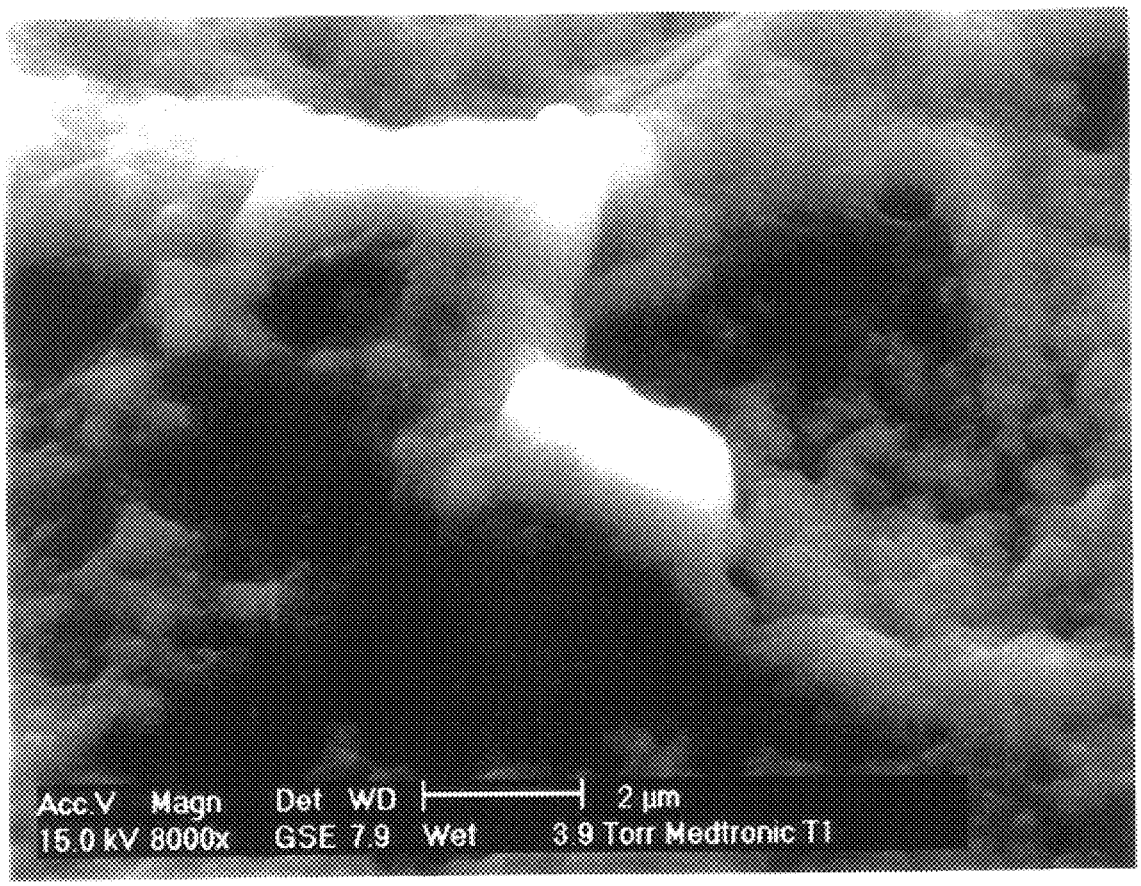
Figure 8K:
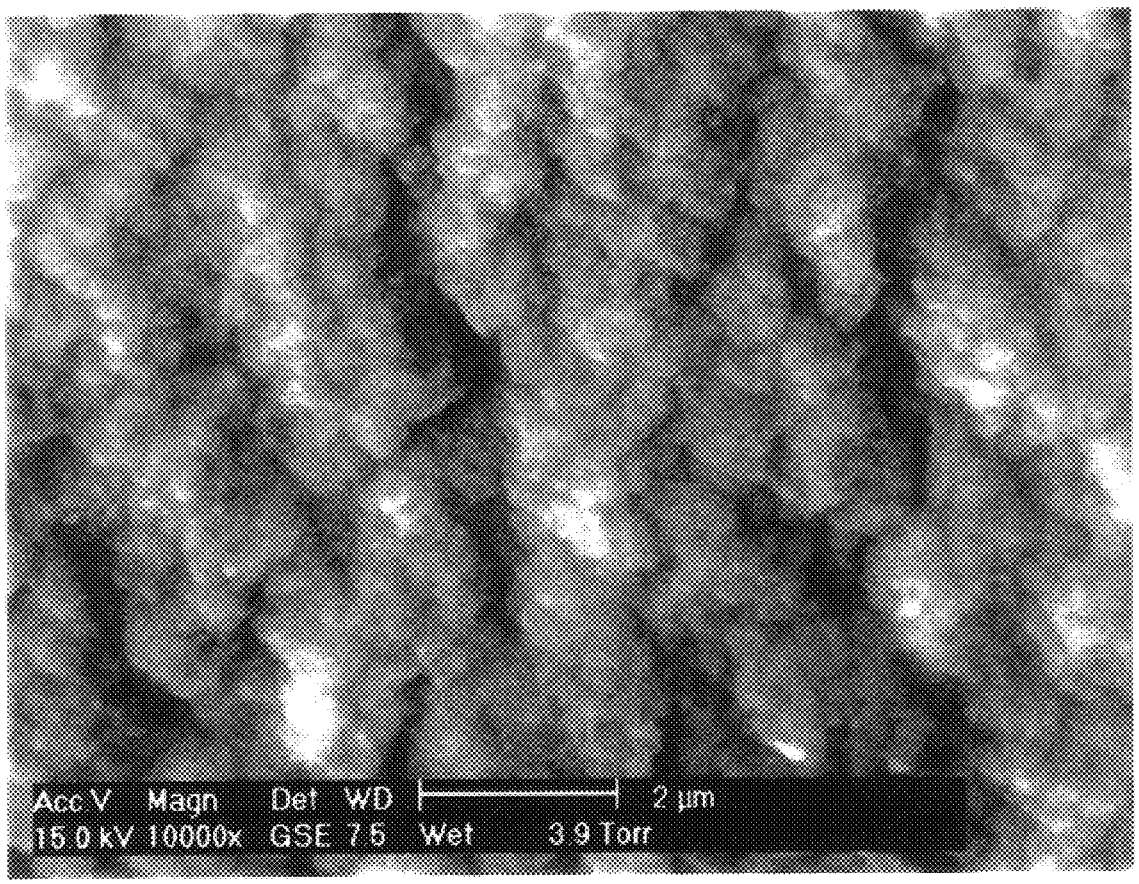

Scanning electron microscopy (FIGS. 8a, 8b, 8f and 8g) was performed on the tubing samples after gold coating. Magnification ranged from 1000× to 15,000× with an accelerating voltage of 5 kV. SEM analysis of tubing samples at 1000× indicated that there were regions of uniform nodular ridges (FIG. 8f) and others where the field contained non-uniform, less distinct ridges as well as particulate-like features (FIG. 8g). A cross-sectional sample was obtained for SEM analysis by simply cutting the tubing with a razor blade by hand and mounting the specimen with the cut side up and roughly parallel to the mounting stub. Cross-sectional SEM (FIG. 8b) images of the treated tubing showed a surface with rounded nodules of low relief consistent with the images that were normal to the tubing surface, and suggested that the depth of the "valleys" was on the order of a tenth of a micron. This was consistent with AFM observation (FIGS. 8c and 8d) where, although the maximum feature height was 0.412 micron, the root mean squared average of heights within the field was only 0.074 micron. The nodular ridges appeared to be rounded rather than sharp or square under all methods of observation.

The results from all three methods were reasonably consistent and indicated that the treated tubing surface exhibited roughly parallel nodular ridges oriented perpendicular to the tubing axis with micron-sized crest-to-crest distances.

The texture on the silicone catheter was also evaluated in wet mode on the Phillips XL30 ESEM-FEG at the Campus Electron Optics Facility at The Ohio State University by Dr. Andreas Von Recum with the help of Mr. Cameron Begg. The operating conditions for the ESEM were an accelerating voltage of 15 kV and a working distance of 8 to 10 mm. The silicone catheter was viewed at the magnifications of 1000× to 10,000×. The sample was scanned to locate a representative area and the SEM images were captured at the noted magnifications.

The ESEM evaluation revealed that the silicone catheter was successfully textured and that the texturing was not uniform (FIGS. 8h, 8i, 8j and 8k). The catheter appeared to be textured in bands in the range of 5 μm. Within the bands, there were surface features in the range of 2 to 3 μm. Additionally, the textured catheter possessed debris particles that appeared to be embedded in the device, which may have been introduced during the molding/texturing process. ESEM analysis of the non-textured control catheter revealed no microtexturing but there were several cracks and debris particles on the control catheter surface.

Example II

Effects of Tubing Tension, Line Speed, and OD Power on Plasma Deposited Texturing of the Outer Diameter (OD) Surface of Silicone Tubing The relative effects of tubing tension, line speed and OD power on the surface features, particularly peak to peak distance of the ridges, of the textured siloxane surface of silicone tubing was investigated.

Materials and equipment.

Silicone tubing (single lumen, ID 0.046 inches, OD 0.068 inches) was obtained from Specialty Silicone Fabricators, Inc. The plasma reactor used in this experiment was as described in Example I. HMDSO was obtained from Aldrich Chemical Company, Milwaukee, Wis.

Plasma deposition.

The plasma reactor was operated in manual mode. Thirty sections of 300 foot length tubing were treated, and tubing tension, line speed, or RF power were varied for each run. Tubing tension was tested at 15, 20, 25, 30, 40, 45, and 55 g; line speed was tested at 20, 30, 35 and 40 inches/minute; and RF power was tested at 40, 50, 60, and 90 watts. Operating parameters that were constant from run to run were: upper orifice diameter, 0.073 inches; ID upper bell jar pressure, 100 mT; ID upper bell jar gas, argon; ID upper bell jar argon flow, 2.00 sccm; ID glass, ID 0.090 inches, OD 0.250 inches, 10 inch length; ID electrode, none; ID zone power, none; ID upper bell jar vapor, none; ID upper bell jar vapor flow, 0.0 sccm; OD zone diffuser, 0.073; OD zone pressure, 100 mT; OD zone co-gas, argon; OD zone argon flow, 9.00 sccm; OD zone vapor source readout, 38.85 T; OD zone vapor, HMDSO; OD zone vapor flow, 0.2 sccm; OD zone glass size, 1½ inch×16 inch; OD zone electrode; DG-300; OD zone power, radio frequency RF5S, 13.56 Mhz, continuous (not pulsed); OD zone RF cable length, standard; manifold pressure, 40 mT; lower drive block sized for tubing; lower bell jar gas, argon; lower bell jar pressure, 100 mT; lower bell jar gas flow rate; 2.0 sccm.

The vacuum pump was started with all valves completely open and all flows off, and allowed to pump down for about four hours. Gas and vapor flows were then initiated and allowed to equilibrate. When all zones were at the predetermined pressures, the reaction was begun and texture was deposited on the tubing as the tension, line speed, and RF power were individually varied over the 30 sections.

Samples from each of the resulting textured 30 tubing sections were examined under a microscope at 650× and representative photographs were taken. These 650× photographs were analyzed by placing a ruler at a location on the photo parallel to the longitudinal axis of the tubing (designated "L" for the longitudinal orientation). The number of "ridges" or micronodules per 2 cm length of the ruler was recorded and entered into Design Expert software (Stat-Ease, Minneapolis, Minn.). The number of ridges intersecting the 2 cm ruler line extending longitudinally on the 650× photographs ranged from 8 to 19. The ruler was then placed in perpendicular to the longitudinal axis of the tubing (designated "T" for the transverse orientation), and the number of "ridges" or micronodules crossing a 2 cm ruler line was recorded as "disorder" which can be viewed as a measure of the randomness and off-axis nature of the ridges. In other words, not all ridges are perpendicular to the longitudinal axis; some are offset with respect to the longitudinal axis, tracing a more spiral-like path. The number of ridges intersecting a ruler placed transverse to the longitudinal axis of the tubing ranged from 1 to 4.

Results.

Figure 9:
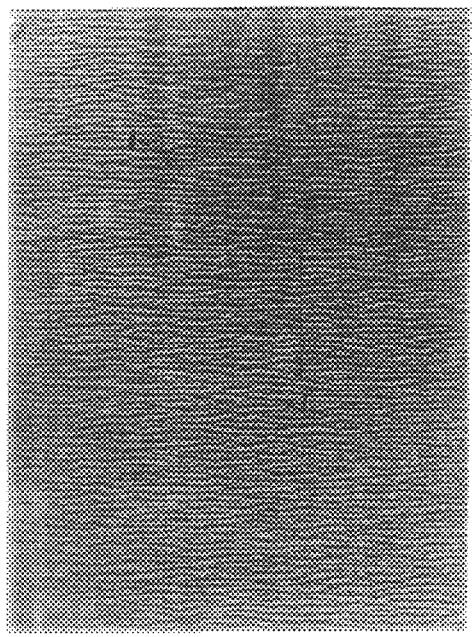
FIG. 9 shows optical microscopy photomicrographs (650×) of silicone tubing having a textured surface according to the invention: (a) 60 W OD power, 40 inches/minute line speed, 15 g tubing tension; (b) 60 W OD power, 40 inches/minute line speed, 45 g tubing tension; (c) 60 W OD power, 20 inches/minute line speed, 15 g tubing tension; (d) 60 W OD power, 20 inches/minute line speed, 45 g tubing tension.
Figure 9:
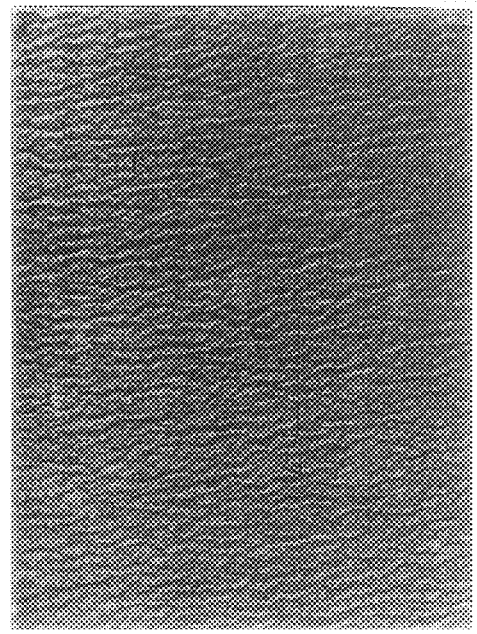
Figure 9:
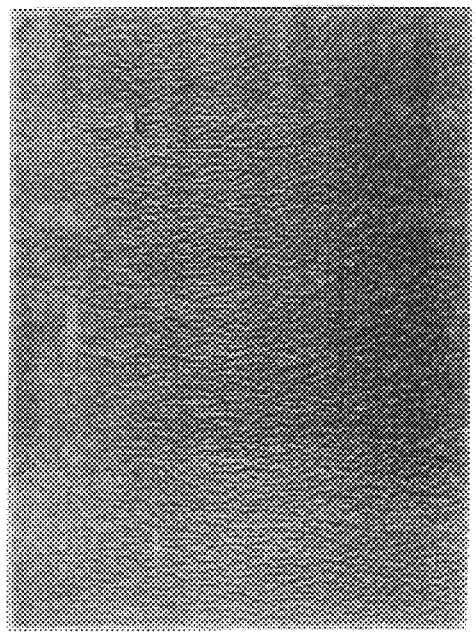
Figure 9:
Figure 9:
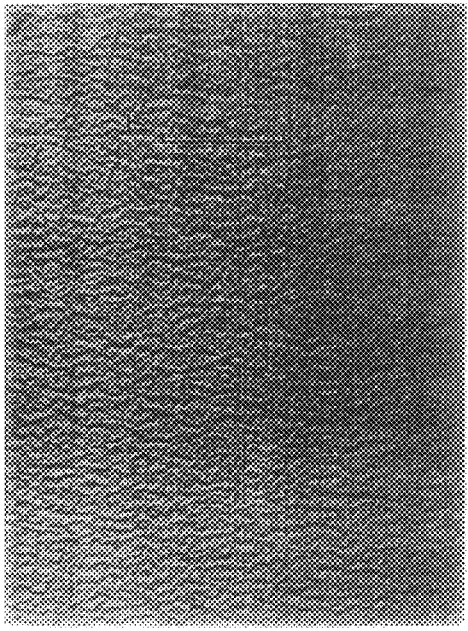

Analysis using Design Expert software indicated that the tubing tension affects the amount of disorder in the pattern of ridges. As tension increased, disorder was lowered. Higher tension created ridges that tended to be straighter and closer to 90 degrees (i.e., perpendicular) with respect to the longitudinal axis. This is especially true for faster line speeds. FIG. 9 shows representative sections of tubing textured with low and high tensions and line speed. The approximate scale is 2 mm on photograph is equivalent to 3 $\mu$m actual distance; L=longitudinal, T=transverse.

Ridges/cm was also analyzed in Design Expert and found to fit a model quite well. Adjusted $r^2$=0.73. The results showed that the longitudinal spacing of the ridges (i.e., ridges/cm) is unaffected by tension when the line speed is low (e.g., 20 inches/minute), but at high line speed (40 inches/minute) the ridges/cm increased as speed increased. Variations in RF power appeared to have no effect on feature spacing or alignment. The spacing shown on the photos is in the approximate range of 1 to 3 mm between the ridges.

It was thus demonstrated that a good measure of control is possible over the spacing of surface features created on silicone tubing coated using plasma siloxane depositions.

Example III

Plasma Deposition of Siloxane to Create Texture on an External Surface of Silicone Flat Stock Materials and equipment.

Batch depositions were done in a custom-built RF powered parallel plate plasma reactor 500 as shown in FIG. 10. Plasma reactor 500 consisted of a glass bell jar 510 attached to a base plate 514, housing capacitively coupled electrodes 512. A rotary vane mechanical vacuum pump was connected to glass bell jar 510 using appropriate vacuum plumbing 518. Mass flow controllers were used to meter the flow of monomer and co-gas, in this example argon, from the monomer reservoir through monomer and gas inlet 516 into the reactor between the electrodes. A throttle valve and pressure sensors were used to maintain the pressure in the bell jar 510 to certain set points. Capacitively coupled parallel plate electrodes 512 were connected to an RF power source via an RF power connector 520 powered by an RF generator operating in continuous mode at 13.56 MHz. The powered electrode 522 also served as a sample stage.

Silicone flat stock was plasma treated in (a) a relaxed state (unstretched) and (b) a stretched state in which it was elongated to 150% of its original length. Silicone substrate (Dow Corning Silastic, Medical grade sheeting. ¾×2×0.020 inches) was placed on an insulating sample holder and held at 150% elongation with binder clamps. The prestretched sample assembly, alongside a sample of unstretched silicone, was placed on the substrate rack. The sample rack was loaded into the reactor between the electrodes. The bell jar was placed over the electrodes and the system was evacuated with the mechanical pump to a base pressure of 0.004 Torr. HMDSO and argon were then introduced into the reactor at flow rates of 10.0 sccm and 2.5 sccm, respectively. The pressure was allowed to equilibrate to a set point of 1.0 Torr for 30 minutes. The RF power was to turned (100 Watts) on for the 20 minute deposition. The power and gas flows were turned off and the reactor was brought up to atmospheric pressure.

Results.

Figure 11A:
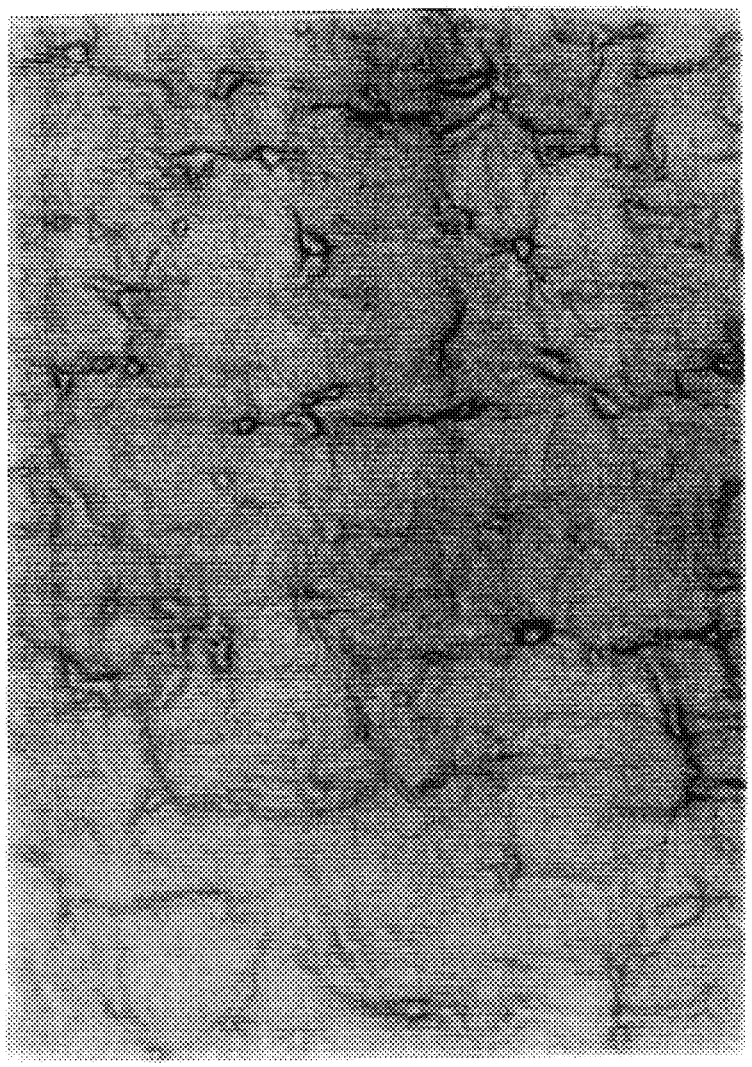
FIGS. 11A and 11B shows optical microscopy photomicrographs (600×) of silicone flat stock having a textured surface according to the invention: (a) unstretched surface; (b) prestretched surface.
Figure 11B:
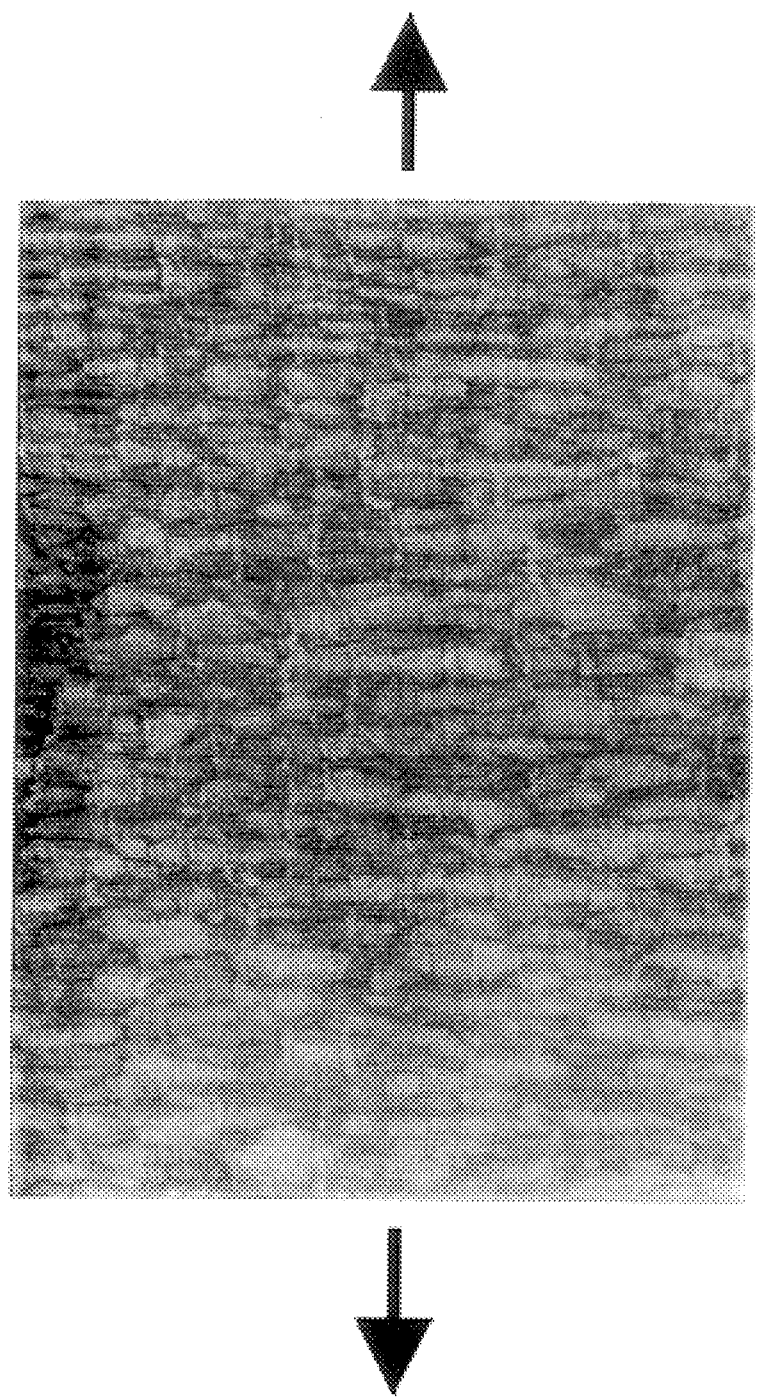

Samples were examined under a microscope at 600× and representative photographs were taken. The photomicrograph of the unstretched sample, FIG. 11(*a*), showed some surface texturing, generally widely spaced and somewhat random. Ridges perpendicular to the stretched direction (arrows indicate the stretched direction in the photomicrograph) were observed in the photo of the stretched sample, FIG. 11(*b*). Stretching the substrate prior to deposition produced ridge features oriented perpendicular to the stretched direction.

Additionally, samples from this deposition and untreated silicone tubing were also analyzed with atomic force microscopy (AFM). Height images were obtained for silicone samples that had been treated in the stretched and unstretched states. These films were deposited using the same conditions as described above (100 Watts, 2.5 sccm Ar, 10.0 sccm HMDSO, 1.0 Torr, 20 minutes deposition time). The height images of both samples showed micron scale surface features; these surface features appeared to be larger than the surface features observed on films deposited onto silicone tubing in a continuous process.

Example IV

Biocompatability Testing of a Surface Treated Silicone Catheter

Dr. Andreas F. von Recum (Ohio State University) was asked to evaluate the subcutaneous healing response of rats to plasma siloxane surface textured silicone lead tubing.

Methods and materials.

Forty (40) contiguous 2.5 cm long samples were cut from single lumen silicone lead tubing (0.057 inches I.D., 0.079 inches O.D.) and from the same tubing after plasma siloxane surface treatment (see Example I). Silastic™ Medical Grade Type A adhesive (Dow Corning Corporation, Midland, Mich., Cat. No. 1051 393-0393) was injected via a syringe and blunt tip needle about 0.5 cm deep into each tubing end. After the plugs had cured for three days at room temperature, the samples were trimmed to 2.0 cm in length. Silastic™ plugs about 0.25 cm deep remained in each end of the tubing samples after trimming. The trimmed tubing samples were cleaned substantially as described in S. Rowland, *J. Applied Biomaterials*, 6:1–7, (1995).

Catheter implantation.

Using sterile techniques, 14 control silicone catheter specimens and 12 treated (textured) silicone catheter specimens were implanted into the dorsal subcutaneous tissue of 6 rats. All of the implants were sterile and individually packed by the respective manufacturer.

The animals were singly housed prior to and after surgery in the small animal facility in Postle Hall at The Ohio State University in order to eliminate complications.

The six male Sprague-Dawley rats weighed 250 to 300 g each. Anesthesia was induced by using ketamine/xylazine i.p., which was administered by a veterinary technician. The dorsal region from the shoulder blade to the base of the tail of the anesthetized rat was clipped and swabbed with iodine and ethanol. Two longitudinal incisions approximately 1 inch in length along the midline of the back were made in rats #1–5 and three 1 inch incisions were made on rat #6. Two small tissue pockets were created on either side of each incision in the latero-ventral direction. One implant was placed in each pocket created. Therefore, rats #1–5 received 4 implants, i.e., 2 treated (T) and 2 untreated (C1 for control tubing that was identical to the treated tubing except that it was not surface-textured; C2 for a different control). In addition to receiving these 4 implants, rat #6 received 2 additional Dacron cuff control implants. After inserting one specimen into each separate pocket, the incision was sutured. The different implants were randomly assigned to one of the 4 implantation sites, sites A and B being associated with the proximal longitudinal incision, and sites C and D being associated with the distal longitudinal incision (see Table 1).

TABLE 1

| Rat Number, Implant Placement and Type of Implant |
|---|
| Rat 1-A (T) |
| Rat 1-B (C1) |
| Rat 1-C (T) |
| Rat 1-D (C2) |
| Rat 2-A (C1) |
| Rat 2-B (C2) |
| Rat 2-C (T) |
| Rat 2-D (T) |
| Rat 3-A (T) |
| Rat 3-B (C2) |
| Rat 3-C (C1) |
| Rat 3-D (T) |
| Rat 4-A (T) |
| Rat 4-B (T) |
| Rat 4-C (C2) |
| Rat 4-D (C1) |
| Rat 5-A (C2) |
| Rat 5-B (T) |
| Rat 5-C (C1) |
| Rat 5-D (T) |
| Rat 6-A T |
| Rat 6-B T |
| Rat 6-C (C2) |
| Rat 6-D (C1) |
| Rat 6-E (Dacron cuff) |
| Rat 6-F (Dacron cuff) |

It is important to note that since only one incision was made and two tissue pockets were created, it was postulated that the specimen might experience some movement during and post implantation. In an attempt to prevent this, subcutaneous sutures were used in addition to skin sutures.

The rats were single-housed following the surgery. Fourteen days following implantation, the skin sutures were removed. The skin incisions had healed per primam, the implants could be palpated and had no signs of fluid accumulation or infection.

Catheter explantation.

The length of implant residence was 43 days. The six male Sprague-Dawley rats were euthanized by a veterinary technician, sequentially, in a $CO_2$ chamber minutes before the implant explantation. The implants were removed by cutting through the subcutaneous tissue with a scalpel, and the membrane surrounding the implant was not disturbed. The implant and its surrounding tissue was dissected off of the skin by sharp and blunt dissection, placed on an index card, and then placed in 10% formalin in a French Square and fixed for 10 days. In a few cases, the implants had migrated after implantation and were seated next to each other. In these cases, the 2 implants were removed together as one unit and fixed as described above (i.e., the implants were not separated).

Gross observations of explants.

In general, the implants were sitting on the fascia with minimal fat in between.

In rat 1, implants A and B had migrated after implantation, so they were found next to each other. Implants A, B, and C were surrounded by a clear membrane. Implant D had several surrounding blood vessels and its membrane was slightly yellowish. This membrane appeared to be thicker than the membranes surrounding implants A, B, and C.

In rat 2, implants A, C, and D had a clear membrane. The membrane surrounding implant B was opaque and appeared to be somewhat thicker.

In rat 3, implants A and B had migrated after implantation so they were seated next to each other. There were several blood vessels next to and on top of implants A and B. These implants had an opaque membrane with a slightly yellow tinge to it. Implant C and D appeared to have a clear but thinner membrane.

In rat 4, implants A and B had migrated and were seated together. Implants A, B, and D had a clear membrane surrounding them. Implant C had several blood vessels supplying it. This implant membrane was opaque and slightly yellow.

In rat 5, implant A appeared to have a clear membrane. Implant B was slightly yellow and the surrounding membrane appeared to be thicker with many blood vessels surrounding it. Implants C and D had migrated together. The membrane surrounding them appeared to be clear.

In rat 6, the implants A, B, and D were each surrounded by a clear membrane. Implant C had a slightly yellow membrane with several surrounding blood vessels. Implants E and F had an opaque, yellowish membrane with many surrounding blood vessels.

Histological preparation of explants.

After fixation, the samples were trimmed for embedding. The specimens were then placed in the tissue processor where they were dehydrated and cleared. The specimens were dehydrated in the following process: 70% ethanol for 2 hours, 95% ethanol for 1 hour, absolute ethanol for 1 hour, and absolute ethanol for 1.5 hours. The specimens were cleared in toluene reagent for 1 hour, toluene for 1.5 hours, paraffin for 1 hour, paraffin for 1 hour, and then held in paraffin until embedding. The specimens were embedded in Stephens Scientific Type 9 Tissue Embedding Media (Melting Point: 55–57 C). The catheters and their respective tissue capsules were embedded perpendicular to the embedding paraffin, so that upon sectioning a cross-section of the catheter and its capsule would be obtained. Routine histological sectioning was performed on a Leitz Rotary Microtome Model 1512 at 5 to 6 microns. Following the sectioning, the specimen sections were stained in routine Hematoxylin & Eosin (H&E) and Masson's Trichrome (a general collagen stain).

Results.

The specimens sections were examined under a Zeiss or Olympus microscope at 40×magnification. The sections were examined for three parameters which determine histocompatibility: the thickness of the fibrohistiocytic interface, the thickness of the fibrous capsule, and granulocytic inflammation. The fibrohistiocytic interface (FHCI) is the presence of cells of macrophage and/or fibroblast phenotype between the catheter and adjacent tissue. The fibrous capsule (FC) is the presence of fibrocytes and collagen directly surrounding the catheter or FHCI. Granulocytic inflammation (GI) is the presence of polymorphonuclear leukocytes in either the FHCI or FC. Four readings were taken on each specimen at approximately 90 degree angles. Each specimen was given a grade from 0 to 2 for each of these three parameters by two examiners, according to the grading scale in Table 2. The examiners read the histological sections independently.

TABLE 2

Grading Scale for Determining Silicone Catheter Biocompatibility

| Biocompatibility Parameter | Grading Key |
| --- | --- |
| Fibrohistiocytic Interface (FHCI) | 0: not present |
| | 1: 1 to 3 cell layers thick |
| | 2: greater than 3 cell layers thick |
| Fibrous Capsule (FC) | 0: not present |
| | 1: 1 to 10 cell layers thick |
| | 2: greater than 10 cell layers thick |
| Granulocytic Inflammation (GI) | 0: not present |
| | 1: 1 to 10 cells at 40x |
| | 2: greater than 10 cells at 40x |

Out of the eighteen catheters, one catheter was disregarded from the study due to extensive granulocytic inflammation presumed due to infection. Therefore, the statistical analysis was performed on the 17 catheters (i.e., 6 control and 11 treated catheters). For the fibrohistiocytic interface, the textured catheter had a borderline significantly higher value than the control catheter with a p-value of 0.0423. For the fibrous capsule, the textured catheter had a significantly lower value than the control catheter with a p-value of 0.0286. For the granulocytic inflammation, the treated catheter did not have a statistically significant effect, since the p-value is 0.2324.

The statistical analysis was performed again using the actual cellular counts (raw data for one examiner) for the three histocompatibility parameters and not the grading scale numbers (0 to 2) to compare with the above results. The results of the raw data were in complete agreement with the results shown above, demonstrating that the grading scale did not lose any information pertaining to the histological response of the catheters.

The results demonstrate that texturing a silicone catheter does improve its histological response. First, the textured catheters had a significantly lower fibrous capsule thickness than the control (untextured) catheters. Since capsule thickness relates to interfacial stress transfer, it appears that the texture allowed tissue adhesion and improved stress transfer. Second, as expected, there were no significant differences in the number of granulocytic inflammatory cells with the capsules of either type of catheter. Granulocytic inflammatory cells within the capsule tend to reflect material compatibility, and both the textured and control catheters were made from the same material (silicone). Third, the textured catheters had a borderline significantly greater fibrohistiocytic interface than the control catheters. Fibrohistiocytic cells at the interface may be seen as indicators of the nature of the surface texture (e.g., regularity, uniformity, and feature sharpness).

Conclusion.

Surface microtexture on a silicone catheter can improve its histocompatibility. In spite of the small number of implanted animals, the textured catheter had a statistical significantly lower fibrous capsule thickness, no significant difference in the number of granulocytic inflammatory cells, and a borderline significantly higher fibrohistiocytic interface thickness as compared with the control (untextured) catheter. The results of the study confirm that the surface texture is not only harmless to the adjacent tissue, but actually improves the desired tissue response through tissue attachment to the polymeric surface.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to textured silicone tubing. The present invention is also not limited to a textured elongate elastomeric surface per se, but may find further application as a textured elastomeric surface, planar or nonplanar, of any desired shape. Nor is the present invention limited to structures or devices for medical use as described herein; the textured surfaces of the present invention find application in a variety of settings, including the packaging industry, automotive industry, and the like. The textured surfaces of the invention are generally useful as an anti-stick or an anti-blocking coating, and can serve generally as a release coating for any type of application that involves the formation of a releasable seal. The present invention further includes within its scope methods of making and using the textured surfaces described hereinabove.

We claim:

1. A method of texturing an external surface of an elongate elastomeric substrate for a medical lead, comprising:

stretching the elongate elastomeric substrate to yield a prestretched elongate elastomeric substrate;

continuously moving the prestretched elongate elastomeric substrate through a plasma deposition chamber; and depositing at least one reactant monomer on at least one external surface of the prestretched elongate elastomeric substrate to form texture said external surface as the prestretched elongate elastomeric substrate moves through the plasma deposition chamber.

2. The method of claim 1, wherein the elongate elastomeric substrate comprises silicone and the prestretched elongate elastomeric substrate is moved through the plasma deposition chamber at a line speed of about 5 inches per minute to about 100 inches per minute.

3. The method of claim 1, wherein the elongate elastomeric substrate comprises silicone and is stretched by applying a tension of about 5 grams to about 100 grams to yield the prestretched elongate elastomeric substrate.

4. The method of claim 1, wherein the elongate elastomeric substrate comprises at least one material selected from the group consisting of silicone, polyurethane, polyisoprene and natural rubber.

5. The method of claim 4, wherein the elongate elastomeric substrate is silicone tubing.

6. The method of claim 1, wherein the reactant monomer comprises at least one of a siloxane and a silane.

7. The method of claim 6, wherein the reactant monomer comprises a siloxane selected from the group consisting of hexamethyldisiloxane (HMDSO), tetramethyidisiloxane (TMDSO) octamethylcyclotetrasiloxane, tetramethylcyclotetrasiloxane and hexamethylcyclotrisiloxane.

8. The method of claim 7, wherein the elongate elastomeric substrate is silicone tubing.

9. The method of claim 1, further comprising plasma pretreating the elongate elastomeric substrate prior to depositing the reactant monomer.

10. The method of claim 1, further comprising incorporating a bioactive molecule onto the textured external surface of the elongate elastomeric substrate.

11. The method of claim 1, wherein the surface texture comprises a multiplicity of micron scale surface features characterized by controlled spacing along the longitudinal axis of the elongate elastomeric substrate.

12. A method of making an elongate elastomeric structure for a medical lead, the elongate textured structure comprising a textured external surface, comprising:

stretching the elongate elastomeric structure to yield a prestretched elongate elastomeric structure;

continuously moving the prestretched elongate elastomeric structure through a plasma deposition chamber; and depositing at least one reactant monomer on at least one external surface of the prestretched elongate elastomeric structure to form texture said external surface as the prestretched elongate elastomeric structure moves through the plasma deposition chamber to yield an elongate elastomeric structure comprising a textured external surface.

13. The method of claim 12, further comprising incorporating a bioactive molecules onto the textured external surface of the elongate elastomeric substrate to yield an elongate elastomeric structure comprising a textured external surface comprising a bioactive molecule.

14. The method of claim 12, wherein the elongate elastomeric structure comprises all or a portion of a lead or a catheter.

15. A method of texturing an external surface of an elastomeric substrate for a medical lead, comprising:

stretching the elastomeric substrate to yield a prestretched elastomeric substrate; and depositing at least one reactant monomer on at least one external surface of the prestretched elastomeric substrate to form texture said external surface.

16. The method of claim 15, wherein the monomer is deposited for about 1 minute to about 30 minutes.

17. The method of claim 15, wherein the elastomeric substrate comprises silicone.

18. The method of claim 15, wherein the reactant monomer comprises at least one of a siloxane or a silane.

19. A textured elongate elastomeric structure made according to the method of claim 12.

20. The textured elongate elastomeric structure of claim 19, comprising silicone tubing, said textured elongate elastomeric structure having improved slip characteristics compared to non-textured silicone tubing.

21. The textured elongate elastomeric structure of claim 19, further comprising all or a portion of a lead or a catheter.

22. A medical device comprising an elongate elastomeric structure made according to the process of claim 12.

23. The medical device of claim 22, the medical device being selected form the group consisting of a pacemaker, a pacemaker-cardioverter-defibrillator, an implantable neurostimulator, an implantable nerve stimulator, a muscle stimulator, an implantable monitoring device, an implantable fluid handling device, a defibrillator, a cardioverter/defibrillator, a gastric stimulator, a drug pump and a hemodynamic monitoring device.

24. A method for making at least one of a medical lead and a medical catheter, comprising:

stretching elastomeric tubing comprising at least one lumen to yield prestretched elastomeric tubing;

continuously moving the prestretched elastomeric tubing through a plasma deposition chamber; and depositing at least one reactant monomer to form texture on at least one external surface of the tensioned elastomeric tubing as the tubing moves through the plasma deposition chamber, to yield elastomeric tubing having at least one textured external surface;

fabricating the lead or catheter from said elastomeric tubing having the textured external surface.

25. The method of claim 24, wherein the elastomeric tubing comprises silicone tubing.

26. The method of claim 24, wherein the reactant monomer comprises at least one of a siloxane or a silane.

27. The method of claim 24, wherein the textured external surface of the elastomeric tubing comprises a multiplicity of micron scale surface features characterized by controlled spacing along the longitudinal axis of the elastomeric tubing.

28. A method of making at least one of a medical lead and a medical catheter, the lead and catheter having improved slip characteristics, comprising:

stretching silicone tubing comprising at least one lumen to yield prestretched silicone tubing;

continuously moving the prestretched silicone tubing through a plasma deposition chamber; and depositing at least one reactant monomer to form texture on at least one external surface of the prestretched silicone tubing as the tubing moves through the plasma deposition chamber, to yield silicone tubing having at least one textured external surface;

fabricating the lead or catheter from said silicone tubing having the textured external surface.

29. The method of claim 28, wherein the reactant monomer comprises at least one of a siloxane and a silane.

* * * * *